United States Patent
Peters et al.

(10) Patent No.: US 7,772,218 B2
(45) Date of Patent: Aug. 10, 2010

(54) SYNTHESIS OF ANTI-ESTROGENIC AND OTHER THERAPEUTIC STEROIDS FROM 21-HYDROXY-19-NORPREGNA-4-EN-3-ONE

(75) Inventors: Richard H. Peters, San Jose, CA (US); Jyanwei Liu, Sunnyvale, CA (US); John G. Johansson, Menlo Park, CA (US); Kenneth J. Ryan, Sunnyvale, CA (US); Wan-Ru Chao, Sunnyvale, CA (US); Masato Tanabe, Palo Alto, CA (US)

(73) Assignee: SRI International, Menlo Park, CA (US)

( * ) Notice: Subject to any disclaimer, the term of this patent is extended or adjusted under 35 U.S.C. 154(b) by 491 days.

(21) Appl. No.: 10/915,302

(22) Filed: Aug. 9, 2004

(65) Prior Publication Data

US 2005/0009801 A1   Jan. 13, 2005

Related U.S. Application Data

(62) Division of application No. 09/780,990, filed on Feb. 9, 2001, now Pat. No. 6,784,170.

(60) Provisional application No. 60/181,738, filed on Feb. 11, 2000.

(51) Int. Cl.
  *C07J 41/00* (2006.01)
  *C07J 43/00* (2006.01)

(52) U.S. Cl. .................. 514/169; 514/174; 514/178; 552/526; 552/530; 552/531

(58) Field of Classification Search ............... 552/558, 552/526, 530, 531; 514/182, 169, 174, 178
See application file for complete search history.

(56) References Cited

U.S. PATENT DOCUMENTS 2,883,402 A   4/1959   Magerlein et al.
2,925,427 A   2/1960   Djerassi et al.

(Continued)

FOREIGN PATENT DOCUMENTS

EP   0007515   2/1980

(Continued)

OTHER PUBLICATIONS

Bolt et al. (1971), "The 6.alpha.-and 6.beta.-Methyl Steroids in the 19-nor Series," *Recl. Trav. Chim. Pays-Bas* 90(8):849-60 (abstract only).

(Continued)

*Primary Examiner*—Sabiha Qazi
(74) *Attorney, Agent, or Firm*—Isaac M. Rutenberg; Bozicevic, Field & Francis LLP

(57) ABSTRACT

Syntheses of steroids such as 3-hydroxy-7α-methyl-21-[2'-methoxy-4'-(diethylaminomethyl)-phenoxy]-19-norpregna-1,3,5(10)triene citrate ("SR 16234") and analogs thereof are provided, wherein 21-hydroxy-19-norpregna-4-en-3-one serves as a starting material or intermediate. The latter compound may be readily prepared from estrone-3-methyl ether. Certain intermediates in these syntheses also have value as therapeutic agents, for example in the treatment of prostate disorders such as prostatic cancer.

10 Claims, 23 Drawing Sheets

U.S. PATENT DOCUMENTS

| | | | |
|---|---|---|---|
| 3,065,226 | A | 11/1962 | Ringold et al. |
| 3,194,821 | A | 7/1965 | Freiberg et al. |
| 5,116,830 | A * | 5/1992 | Tanabe et al. ............... 514/182 |
| 6,054,446 | A * | 4/2000 | Tanabe et al. ............... 514/176 |
| 6,281,205 | B1 * | 8/2001 | Tanabe et al. ............... 514/176 |
| 6,503,896 | B1 * | 1/2003 | Tanabe et al. ............... 514/182 |
| 6,548,491 | B2 * | 4/2003 | Tanabe et al. ............... 514/182 |
| 6,747,018 | B2 * | 6/2004 | Tanabe et al. ............... 514/169 |
| 6,784,170 | B2 * | 8/2004 | Peters et al. ................ 514/182 |

FOREIGN PATENT DOCUMENTS

| | | | |
|---|---|---|---|
| FR | 2190427 | | 2/1974 |
| FR | 2332759 | | 6/1997 |
| GB | 1277265 | * | 6/1972 |
| JP | 43021058 | | 5/1965 |
| JP | 54112850 A | | 9/1979 |
| JP | 54117454 A | | 9/1979 |
| JP | 54117455 A | | 9/1979 |
| JP | 54117456 A | | 9/1979 |
| WO | WO 99/33859 | | 6/1999 |

OTHER PUBLICATIONS

Fennell et al. (1992), "Effects of Androgen Testosterone 5-Alpha Dihydrotestosterone 19 Nortestosterone Administration on Growth in Turkeys," *Poultry Science* 71(3):539-547 (abstract only).

Gaillard (1991), "Equine Testicular Aromatase Substrates Specificity and Kinetic Characteristics," *Comparative Biochemistry and Physiology B Comparative Biochemistry* 100(1):107-116 (abstract only).

Johnson (1972), "6,6-Difluoro-19-Norprogesterone," *Journal of Medicinal Chemistry* 15(7):784-785.

Kaneko et al. (1969), "Carbalkoxymethylene Steriods," *Chemical Abstracts* 70(19), Abstract No. 88104r.

Krubiner et al. (1966), "The Conversion of 17-Keto Steroids to 20-Olygenated Steroids. A Facile Synthesis of 19-Norprogesterone," *Journal of Organic Chemistry* 31(1):24-26.

Magerlein et al. (1958), "Preparation and Reactions of 11-Substituted 1,3,5(10)-Estratrienes. I. 11-Oxygenated Estrones and Estradiols," *Journal of the American Chemical Society* 80:2220-2225.

Pasman et al. (1982), "Photoinduced Long-Range Electron Transfer in Rigid Bichromophoric Molecules," *Journal of the Royal Netherlands Chemical Society* 101(10):363-364.

Peters et al. (1989), "17-Desoxy Estrogen Analogs," *J. Med. Chem.* 32(7):1642-1652.

Plate et al. (2000), "Synthesis of (3α, 7β, 17α)-7-Methyl-19-Norpregn-5(10)-En-20-Yne-3,7,17-Triol, a Metabolite of ORG OD14, and Its 7-Epimer," *Steroids* 65:497-504.

Sandoval et al. (1955), "Steroids. LCI. Synthesis of 19-Nor-Desoxycorticosterone, a Potent Mineralocorticoid Hormone," *Journal of the American Chemical Society* 77:148-151.

Sih et al. (1968), "Mechanisms of Steroid Oxidation by Microorganisms. XIII. C22 Acid Intermediates in the Degradation of the Cholesterol Side Chain," *Biochemistry* 7(2):796-807.

Skaddan et al. (1999), "Synthesis and Binding Affinities of Novel Re-Containing 7α-Substituted Estradiol Complexes: Models for Breast Cancer Imaging Agents," *J. Org. Chem.* 64(22):8108-8121.

Sundaram et al. (1995), "Different Patterns of Metabolism Determine the Relative Anabolic Activity of 19-Norandrogens," *Journal of Steroid Biochemistry and Molecular Biology* 53(1-6):253-257 (abstract only).

Tedesco et al. (1997), "An Expeditious Route to 7α-Substituted Estradiol Derivatives," *Tetrahedron Letters* 38(46):7997-8000.

Wicha et al. (1977), "Synthesis of Pregn-17/20/-en21-oic Acid Derivatives. The Wittig-Horner Reaction on Steroidal 17-Ketones," *Synthetic Communications* 7(3):215-222.

Wakeling et al. (1988) "Novel Antioestrogens without Partial Agonist Activity" *J. Steroid Biochem.* 31:645-653.

Wakeling et al. (1991) "A Potent Specific Pure Antiestrogen with Clinical Potential" *Cancer Res.* 51:3867-3873.

Wakeling et al. (1990) "Therapeutic Potential of Pure Antioestrogens in the Treatement of Breast Cancer" *J. Steroid Biochem. Moled. Biol.* 37:771-774.

van de Velde et al. (1995) "Exploration of the Therapeutic Potential of the Antiestrogen RU 58668 in Breast Cancer Treatment" *Ann. N.Y. Acad. Sci.* 761:164-175.

Nique et al. (1995) "Antineoplastic, Pure Antiestrogen" *Drugs Future* 20:362-366.

\* cited by examiner

SYNTHESIS OF ANTI-ESTROGENIC AND OTHER THERAPEUTIC STEROIDS FROM 21-HYDROXY-19-NORPREGNA-4-EN-3-ONE

CROSS-REFERENCE TO RELATED APPLICATIONS

This application is a divisional of U.S. patent application Ser. No. 09/780,990, filed Feb. 9, 2001, now U.S. Pat. No. 6,784,170, which claims priority under 35 U.S.C. §119(e)(1) to provisional U.S. Patent Application Ser. No. 60/181,738, filed Feb. 11, 2000, both incorporated herein in their entireties.

TECHNICAL FIELD

This invention relates generally to the chemical synthesis of steroids, and more particularly relates to the synthesis of anti-estrogenic and other therapeutic steroids such as 3-hydroxy-7α-methyl-21-[2'-methoxy-4'-(diethylaminomethyl)-phenoxy]-19-norpregna-1,3,5(10)triene citrate ("SR 16234") and analogs thereof. The invention additionally relates to starting materials and intermediates useful in conjunction with the novel synthesis.

BACKGROUND

Breast cancer is one of the most prevalent types of cancer, and epidemiological and clinical studies have shown that approximately two-thirds of breast tumors are estrogen-dependent. This means that estrogens are required for the growth of such breast tumors in both premenopausal and postmenopausal patients. In postmenopausal women, in whom breast cancer most commonly occurs, breast tumor concentrations of estrone and estradiol are considerably higher than blood estrogen levels. Although retention of estrogens in breast tumors by high-affinity binding proteins contributes to the level of estrogens in tumors, estrogen concentrations in the breast are higher than plasma levels in breast cancer patients regardless of whether their tumors are estrogen receptor-positive (ER+) or estrogen receptor-negative (ER−). In situ formation of estrogen from estrogen biosynthetic precursors within tumors is now known to make a major contribution to the estrogen content of breast tumors.

Numerous other estrogen-dependent conditions, disorders, and diseases have been identified as well, including, but not limited to, ovarian, uterine and pancreatic cancers, galactorrhea, McCune-Albright syndrome, benign breast disease, and endometriosis.

Estrogenic effects are mediated by specific receptors located in the nucleus of estrogen-responsive cells. The receptor contains a hormone-binding domain for binding estrogen, transcription activating domains, and a DNA binding domain. The binding of the receptor-hormone complex to estrogen response elements (ERE's) in the DNA of target genes is necessary for regulating gene transcription.

Drugs that competitively block estrogen binding to its receptor, termed anti-estrogens, are capable of inhibiting the stimulatory effects of the hormone on cell proliferation and are therefore useful in the clinical treatment of breast cancer. Clinically, estrogen receptor-positive tumors respond with a higher frequency to anti-estrogens than do tumors lacking a significant level of receptors.

Anti-estrogenic drugs fall into two chemical classes: nonsteroidal and steroidal. The nonsteroidal anti-estrogen tamoxifen (Nolvadex□) has been used as an adjunctive treatment for breast cancer following chemotherapy or radiation therapy. However, tamoxifen itself exhibits estrogenic activity in reproductive tissue, resulting in an increased risk of endometrial cancer and possible recurrence of breast cancer after long-term therapy. Furthermore, tamoxifen behaves only as a partial agonist in the uterus.

To date, little work has been done in the development of selective competitive antagonists of estrogen. Several steroidal anti-estrogens have been synthesized which lack estrogenic activity. Included among these are ICI 164,384, ICI 182,780 and RU 58668. See, e.g.: Wakeling et al. *J. Steroid Biochem.* 31:645-653 (1988), which pertains to ICI 164,384; Wakeling et al., *Cancer Res.* 51:3867-3873 (1991), and Wakeling et al., *J. Steroid Biochem. Molec. Biol.* 37:771-774 (1990), which pertain to ICI 182,780; and Van de Velde et al., *Ann. N.Y. Acad. Sci.* 761:164-175 (1995), Van de Velde et al., *Pathol. Biol.* 42:30 (1994), and Nique et al., *Drugs Future* 20:362-366 (1995), which relate to RU 58668. Unfortunately, these drugs are not orally active and must be administered in high doses intramuscularly. Furthermore, the manufacture of these drugs is laborious, requiring a complicated, 14-16 step synthesis with very low overall yields. Potent steroidal anti-estrogens that are orally active have not yet been developed or commercialized, although the nonsteroidal mixed agonist/antagonist "raloxifene" is currently available.

Accordingly, steroidal active agents have recently been developed that are extremely effective anti-estrogenic agents, i.e., are potent antagonists of estrogen in breast and/or uterine tissue. The active agents are described in co-pending, commonly assigned U.S. patent application Ser. No. 08/998,877, filed Dec. 24, 1997, now U.S. Pat. No. 6,054,446, and U.S patent application Ser. No. 09/220,408, filed Dec. 23, 1998, (now U.S. Pat. No. 6,281,205) as well as in PCT Publication No. WO 99/33859, published Jul. 8, 1999. These active agents represent a significant advance in the art, particularly in the treatment of breast cancer and other diseases and conditions that are potentiated by the presence of estrogens. A number of those active agents have also been found to display tissue-selective pharmacology and are thus useful as tissue-selective estrogen agonists/antagonists, also termed "Selective Estrogen Receptor Modulators" or "SERMs." SERMs produce beneficial estrogen-like effects in some respects, notably on bone and lipid metabolism, while nevertheless acting as estrogen antagonists in the breast and/or uterus. The SERM profile may be distinguished from that of a pure estrogen such as 17β-estradiol, which behaves as an estrogen agonist in all tissues, and from that of a pure anti-estrogen, which exhibits an estrogen antagonist profile in all tissue types.

An exemplary and representative anti-estrogen in the aforementioned group is the citrate salt of 3-hydroxy-7α-methyl-21-[2'-methoxy-4'-(diethylaminomethyl)-phenoxy]-19-norpregna-1,3,5(10)triene, developed at SRI International (Menlo Park, Calif.) and also referred to herein as "SR 16234." SR 16234 can be represented as follows:

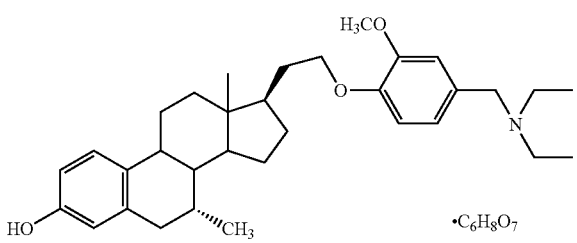

SR 16234 has been found to have potent antitumor activity with remarkable tissue-selective properties: complete antagonist-antiestrogenic activity in human breast tumor cells; complete anti-uterotrophic antagonist activity in rat and human uterine tissue; agonist-estrogenic activity in the cardiovascular system, as reflected in lowered low-density lipoprotein (LDL) and increased high-density lipoprotein (HDL) cholesterol levels in rats; and agonist-estrogenic activity in the skeletal system, as manifested by maintenance of bone and prevention of bone loss in rats. In addition, SR 16234 has been established to have good oral bioavailability, absorption and half-life, with sufficient uptake to sustain therapeutically effective plasma levels of the drug.

Currently, SR 16234 is synthesized using a nine-step synthetic procedure as outlined in FIG. 1. While the synthesis is effective and provides the product in a reasonable overall yield, it would be desirable to provide a simpler, more straightforward synthesis so as to reduce cost (synthesizing SR 16234 using the method of FIG. 1 is quite expensive), to improve overall yield, to avoid use of highly toxic reagents, and to avoid costly and difficult reaction steps such as aromatization with $CuCl_2$.

SUMMARY OF THE INVENTION

Accordingly, the invention is directed to a new method for synthesizing SR 16234 and substituted analogs thereof, which is simpler, more straightforward and more cost-effective than previous synthetic methods, avoids the use of highly toxic reagents, and furthermore avoids costly materials and difficult reaction steps.

It is another object of the invention to provide such a method that employs 21-hydroxy-19-norpregna-4-en-3-one or a substituted analog thereof as a starting material or intermediate.

It is still another object of the invention to provide intermediate compounds and synthetic steps useful in conjunction with the aforementioned syntheses.

It is still another object of the invention to provide certain of such intermediate compounds as therapeutic agents, e.g., in the treatment of prostate disorders such as prostatic cancer.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Figure 1:
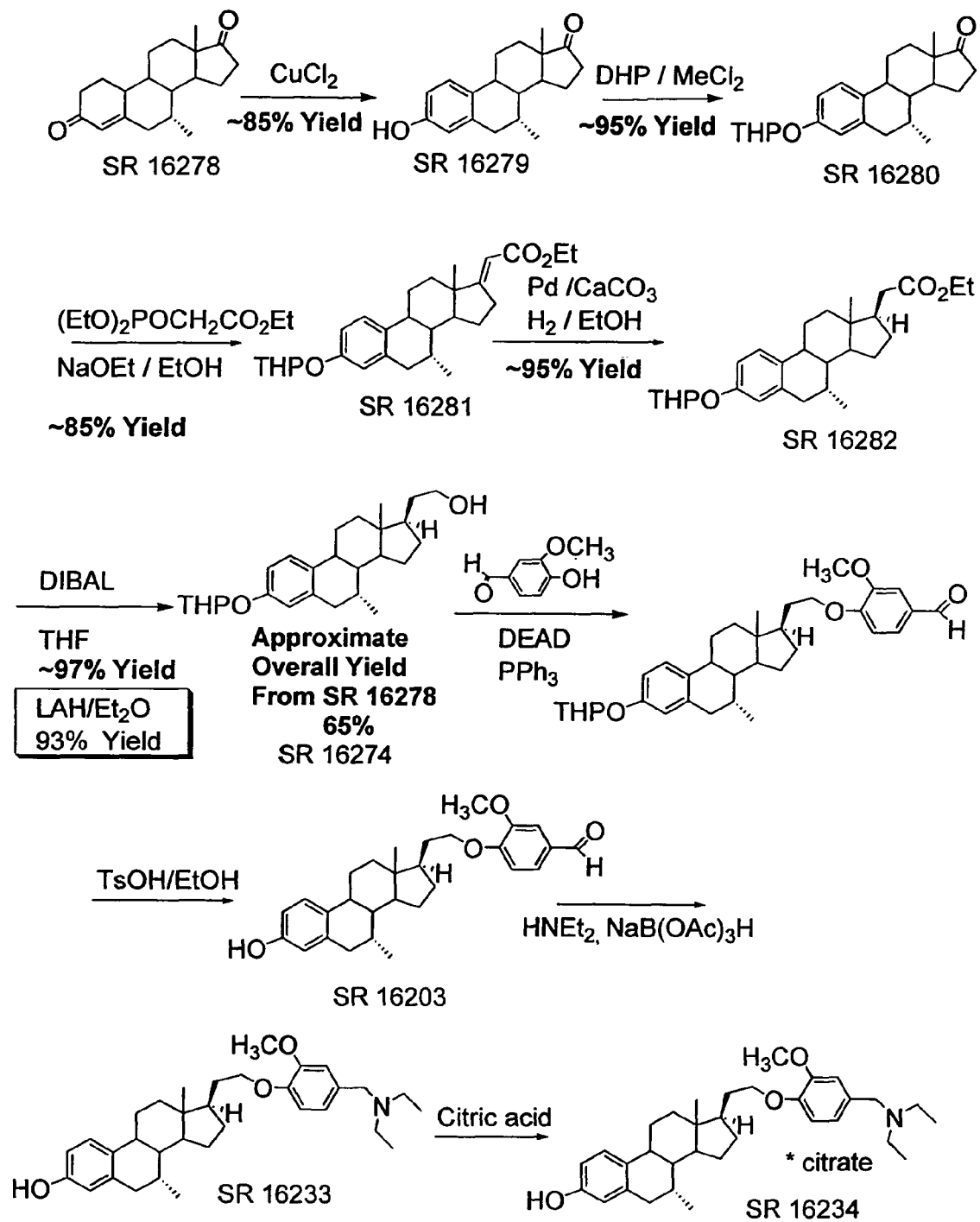
FIG. 1 is a synthetic scheme illustrating a prior method for synthesizing SR 16234.

Definitions:

It is to be understood that unless otherwise indicated, this invention is not limited to specific starting materials, reagents or reaction conditions, as such may vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise.

In this specification and in the claims that follow, reference will be made to a number of terms that shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl, and the like. The term "lower alkyl" intends an alkyl group of one to six carbon atoms, preferably one to four carbon atoms. The term "cycloalkyl" as used herein refers to a cyclic hydrocarbon of from 3 to 8 carbon atoms, such as cyclopropyl, cyclobutyl, cyclopentyl, cyclohexyl, cycloheptyl, and cyclooctyl.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of two to six carbon atoms, preferably two to four carbon atoms. The term "cycloalkenyl" intends a cyclic alkenyl group of three to eight, preferably five or six, carbon atoms.

The term "alkynyl" as used herein refers to a branched or unbranched hydrocarbon group of 2 to 24 carbon atoms containing at least one triple bond, such as ethynyl, n-propynyl, isopropynyl, n-butynyl, isobutynyl, octynyl, decynyl, and the like. Preferred alkynyl groups herein contain 2 to 12 carbon atoms. The term "lower alkynyl" intends an alkynyl group of two to six carbon atoms, preferably two to four carbon atoms.

The term "alkylene" as used herein refers to a difunctional branched or unbranched saturated hydrocarbon group of 1 to 24 carbon atoms, such as methylene, ethylene, n-propylene, n-butylene, n-hexylene, decylene, tetradecylene, hexadecylene, and the like. The term "lower alkylene" refers to an alkylene group of one to six carbon atoms, preferably one to four carbon atoms.

The term "alkenylene" as used herein refers to a difunctional branched or unbranched hydrocarbon group of 2 to 24 carbon atoms containing at least one double bond, such as ethenylene, n-propenylene, n-butenylene, n-hexenylene, and the like. The term "lower alkenylene" refers to an alkylene group of two to six carbon atoms, preferably two to four carbon atoms.

The term "alkoxy" as used herein intends an alkyl group bound through a single, terminal ether linkage; that is, an "alkoxy" group may be defined as —O-alkyl where alkyl is as defined above. A "lower alkoxy" group intends an alkoxy group containing one to six, more preferably one to four, carbon atoms.

The term "acyl" is used in its conventional sense to refer to a substituent alkyl-C—(O)— wherein alkyl is as defined above. The term "lower acyl" refers to an acyl group wherein the alkyl moiety of the group contains one to six, more preferably one to four, carbon atoms.

The term "aryl" as used herein, and unless otherwise specified, refers to an aromatic species containing 1 to 3 aromatic rings, either fused or linked, and either unsubstituted or substituted with 1 or more substituents typically selected from the group consisting of lower alkyl, lower alkoxy, halogen, and the like. Preferred aryl substituents contain 1 aromatic ring or 2 fused or linked aromatic rings. The term "arylene" refers to a difunctional aromatic species containing 1 to 3 aromatic rings substituted with 1 or more substituents as above. Preferred arylene substituents contain 1 aromatic ring (e.g., phenylene) or 2 fused or linked aromatic rings (e.g., biphenylylene).

The term "aralkyl" refers to an aryl group with an alkyl substituent. The term "aralkylene" refers to an arylene group with an alkyl substituent.

The term "alkaryl" refers to an alkyl group that has an aryl substituent. The term "alkarylene" refers to an alkylene group that has an aryl substituent.

The term "heterocyclic" refers to a five- or six-membered monocyclic structure or to an eight- to eleven-membered bicyclic heterocycle. The "heterocyclic" substituents herein may or may not be aromatic, i.e., they may be either heteroaryl or heterocycloalkyl. Each heterocycle consists of carbon atoms and from one to three, typically one or two, heteroatoms selected from the group consisting of nitrogen, oxygen, and sulfur, typically nitrogen and/or oxygen.

The terms "halo" and "halogen" are used in the conventional sense to refer to a chloro, bromo, fluoro, or iodo substituent. The terms "haloalkyl," "haloalkenyl," or "haloalkynyl" (or "halogenated alkyl," "halogenated alkenyl," or "halogenated alkynyl") refers to an alkyl, alkenyl, or alkynyl group, respectively, in which at least one of the hydrogen atoms in the group has been replaced with a halogen atom.

The term "hydrocarbyl" is used in its conventional sense to refer to a hydrocarbon group containing carbon and hydrogen, and may be aliphatic, alicyclic, or aromatic, or may contain a combination of aliphatic, alicyclic, and/or aromatic moieties. Aliphatic and alicyclic hydrocarbyl may be saturated or they may contain one or more unsaturated bonds, typically double bonds. The hydrocarbyl substituents herein generally contain 1 to 24 carbon atoms, more typically 1 to 12 carbon atoms, and may be substituted with various substituents and functional groups, or may be modified so as to contain ether, thioether, —NH—, —NR, —C(O)—, —C(O)—O—, and/or other linkages.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. Similarly, the phrase an "optionally present" double bond as indicated by a dotted line ----- in the chemical formulae herein means that a double bond may or may not be present, and, if absent, a single bond is indicated.

By "anti-estrogenic" as used herein is meant a compound that tends to inhibit the in situ activity of estrogens such as estradiol, following administration to a mammalian individual. Anti-estrogenic activity can be evaluated in terms of inhibition of estradiol-induced alkaline phosphatase activity in human Ishikawa cells using, for example, the procedures described in Example 40 of PCT Publication No. WO 99/33859.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, a method of "treating" an estrogen-dependent disorder, as the term is used herein, encompasses both prevention of the disorder in a clinically asymptomatic individual and treatment of the disorder in a clinically symptomatic individual. Similarly, a method of "treating" a prostate disorder, as the term is used herein, encompasses both prevention of the disorder in a clinically asymptomatic individual and treatment of the disorder in a clinically symptomatic individual.

By the terms "effective amount" or "pharmaceutically effective amount" of a therapeutic agent are meant a nontoxic but sufficient amount of the agent to provide the desired prophylactic or therapeutic effect. As will be pointed out below, the exact amount required will vary from subject to subject, depending on the species, age, and general condition of the subject, the severity of the condition being treated, and the particular agent and mode of administration, and the like. Thus, it is not possible to specify an exact "effective amount." However, an appropriate "effective" amount in any individual case may be determined by one of ordinary skill in the art using only routine experimentation.

By "pharmaceutically acceptable carrier" is meant a material that is not biologically or otherwise undesirable, i.e., the material may be administered to an individual along with the selected therapeutic agent without causing any undesirable biological effects or interacting in a deleterious manner with any of the other components of the pharmaceutical composition in which it is contained. Similarly, a "pharmaceutically acceptable" salt or a "pharmaceutically acceptable" ester of a novel compound as provided herein is a salt or ester that is not biologically or otherwise undesirable.

In describing the location of groups and substituents, the following numbering system will be employed to conform the numbering of the cyclopentanophenanthrene nucleus to the convention used by the IUPAC or Chemical Abstracts Service:

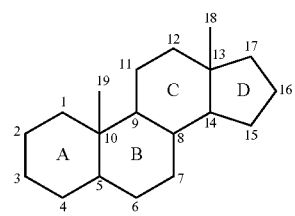

The five- and six-membered rings of the steroid molecule are often designated A, B, C, and D as shown. The term "steroid" as used herein is intended to mean compounds having the aforementioned cyclopentanophenanthrene nucleus.

In these structures, the use of bold and dashed lines to denote particular conformation of groups follows the IUPAC steroid-naming convention. The symbols "α" and "β" indicate the specific stereochemical configuration of a substituent at an asymmetric carbon atom in a chemical structure as drawn. Thus, "α," denoted by a broken line, indicates that the group in question is below the general plane of the molecule as drawn, and "β," denoted by a bold line, indicates that the group at the position in question is above the general plane of the molecule as drawn.

Synthetic Methods:

The synthetic methods of the invention all proceed from estrone-3-methyl ether via 21-hydroxy-19-norpregna-4-en-3-one as an intermediate. It will be understood by those working in the field of steroid chemistry that the cyclopentanophenanthrene nucleus may be substituted with one or more substituents that do not interfere with the synthetic steps described herein.

To prepare the substituted or unsubstituted 21-hydroxy-19-norpregna-4-en-3-one intermediate, a substituted or unsubstituted estrone-3-methyl ether is first converted to a compound having the structural formula (I) by reaction with a triethyl phosphonoacetate or an analogous reagent (see Example 1).

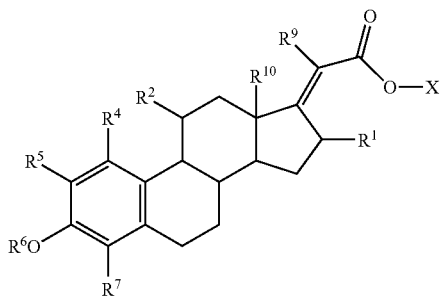

(I)

In structural formula (I):

X is lower hydrocarbyl;

$R^1$ is hydrogen or $CR^{11}R^{12}$, wherein $R^{11}$ and $R^{12}$ are hydrogen or lower alkyl;

$R^2$ is selected from the group consisting of hydrogen, hydroxyl, alkyl, $-OR^{13}$, and $-SR^{13}$ wherein $R^{13}$ is alkyl;

$R^4$, $R^5$, $R^6$, and $R^7$ are independently selected from the group consisting of hydrogen and lower alkyl;

$R^9$ is hydrogen or hydrocarbyl; and $R^{10}$ is methyl or ethyl.

A preferred subset of the aforementioned compounds has the structure of formula (II)

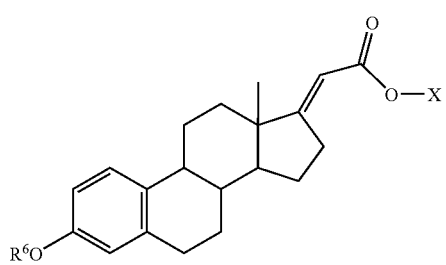

(II)

wherein X is lower alkyl and $R^6$ is hydrogen or lower alkyl.

Figure 2:
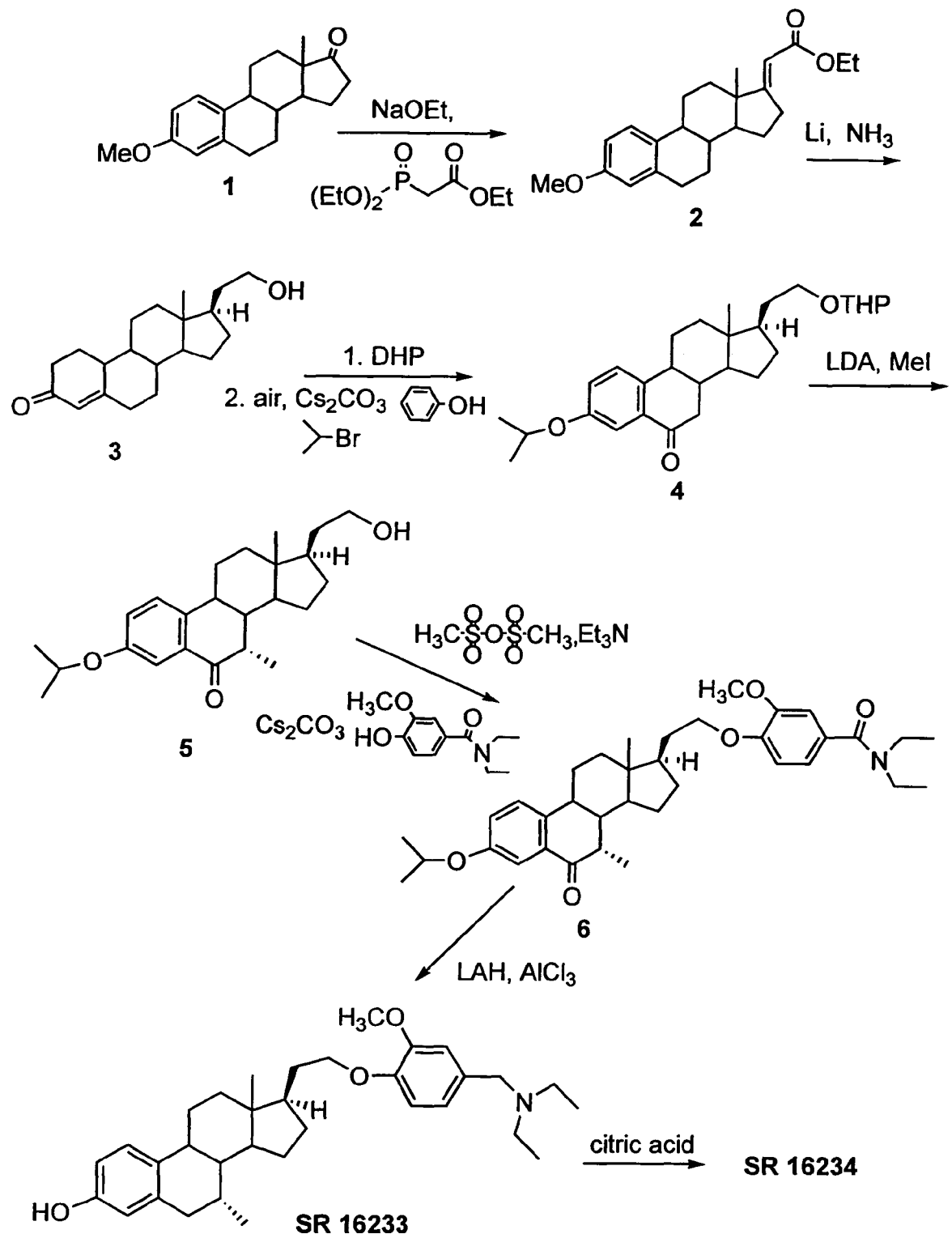
FIGS. 2, 3 and 4 are schemes illustrating methods of the invention for synthesizing SR 16234 from estrone-3-methyl ether (1) via 21-hydroxy-19-norpregna-4-en-3-one (3) as an intermediate.
Figure 3:
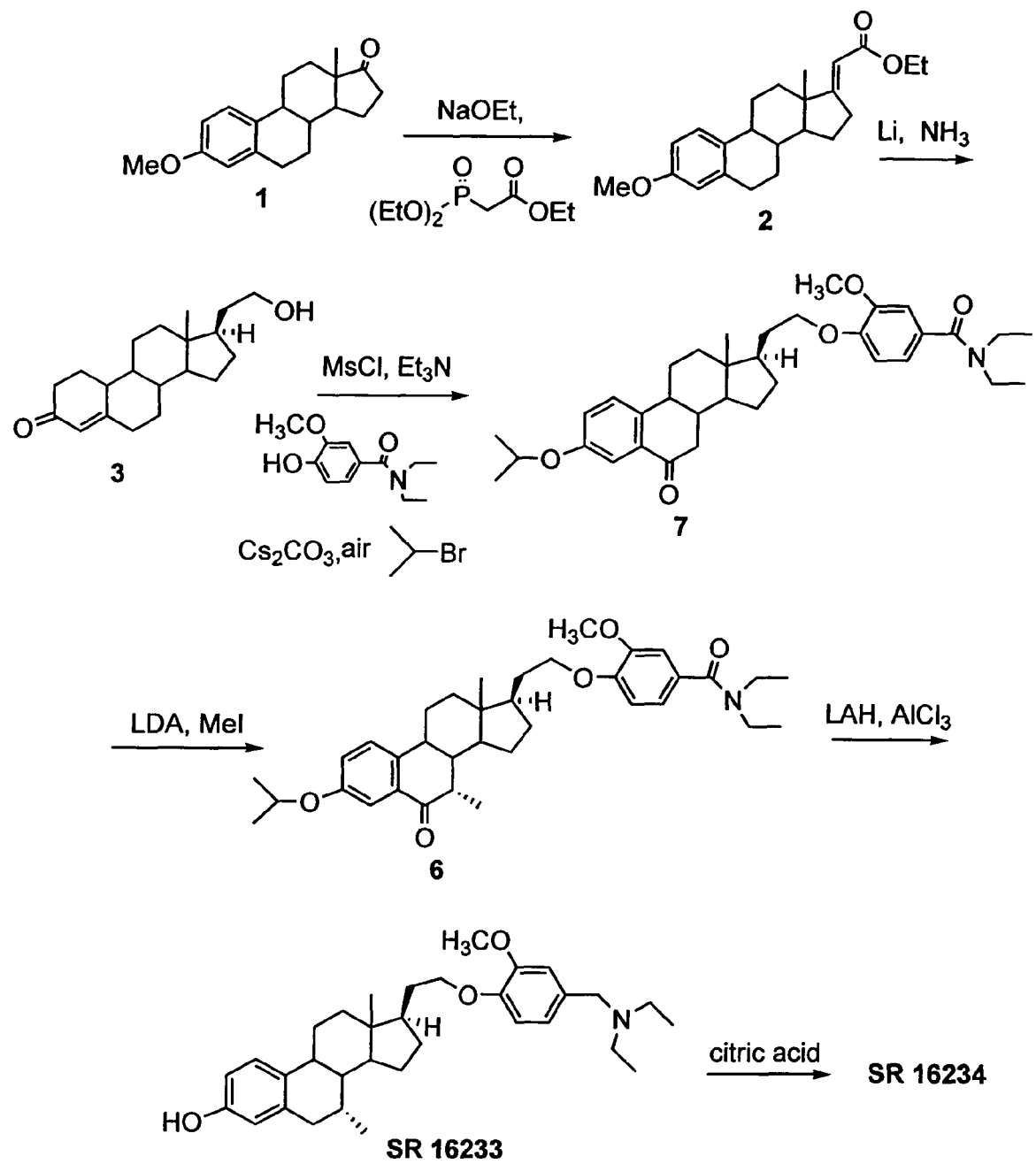
Figure 4:
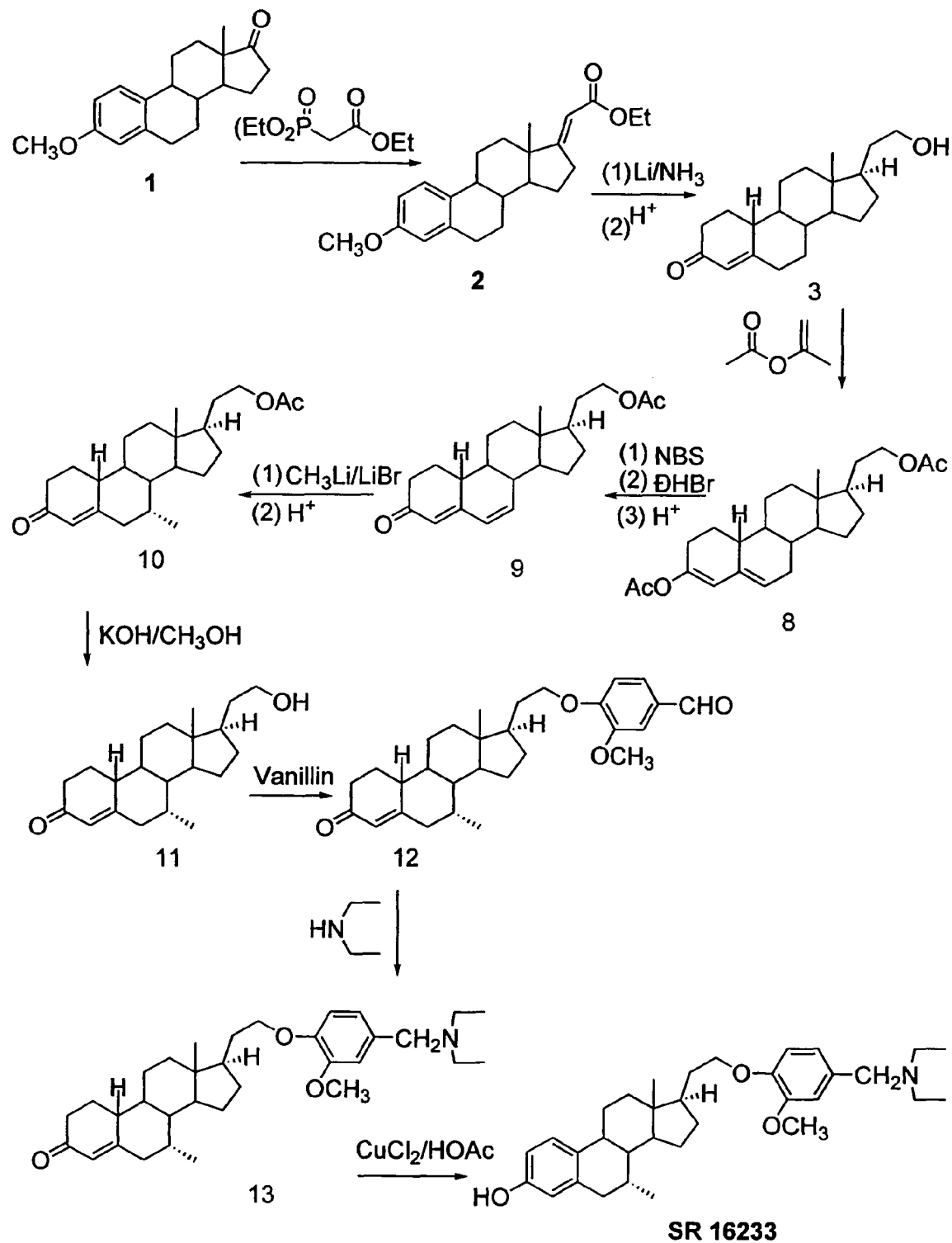

For example, X may be ethyl, and $R^6$ may be methyl (see compound 2 in FIGS. 2, 3, and 4).

In order to convert compound (I) to the substituted or unsubstituted 21-hydroxy-19-norpregna-4-en-3-one intermediate (III)

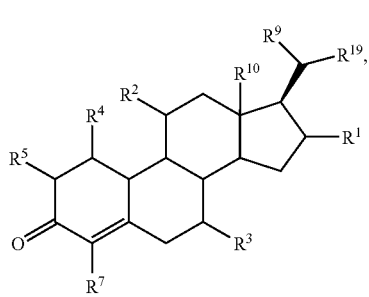

(III)

compound (I) is treated with an alkali metal and ammonia or an alkylamine using known reaction conditions appropriate for a Birch reduction; see, e.g., March et al., *Advanced Organic Chemistry, Fourth Edition* (N.Y.: Wiley, 1992), section 5-10 and references cited therein. Suitable alkali metals include lithium, potassium and sodium, and the reaction preferably takes place in liquid ammonia and optionally in the presence of an alcohol.

In compound (III):

$R^1$, $R^2$, $R^4$, $R^5$, $R^7$, $R^9$, and $R^{10}$ are as defined for formula (I), $R^3$ is hydrogen or hydrocarbyl, typically hydrogen or alkyl, preferably hydrogen or lower alkyl such as methyl, and $R^{19}$ is hydroxyl, hydroxymethyl ($CH_2OH$), protected hydroxyl, protected hydroxymethyl, activated hydroxyl, or activated hydroxymethyl. By "activated" is meant that a hydroxyl group is modified so as to enable reaction with an incoming nucleophile; generally, this means that a hydroxyl group —OH is converted to an —O-LG moiety wherein LG is a leaving group. Activation can involve, for example, reaction with MsCl, TsCl, $SOCl_2$, $SOBr_2$, or the like ("Ms" meaning mesyl and "Ts" meaning tosyl). By "protected" is meant that the hydroxyl group will not undergo reaction in a particular step, but by virtue of a protecting group Pr, the —O—Pr moiety remains intact and can be treated, e.g., with base or acid, to regenerate the unprotected hydroxyl group following reaction. Suitable hydroxyl-protecting groups at the latter position include, but are not limited to, Ms, Ts, acetyl (Ac), and tetrahydropyranyl (THP). It is to be understood that the above-indicated activating and protecting moieties may be used as either protecting groups or activating groups depending on the specific reaction condition.

Preferred intermediates encompassed by structural formula (III) have the structure of formula (IV)

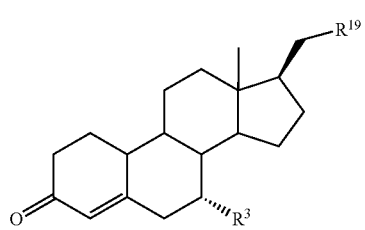

(IV)

wherein:

$R^3$ is hydrogen or lower alkyl; and $R^{19}$ is hydroxyl, hydroxymethyl, protected hydroxyl, or protected hydroxymethyl.

In a representative and specific example of the foregoing reaction, a method for synthesizing 21-hydroxy-19-norpregna-4-en-3-one is provided which comprises treating (IX)

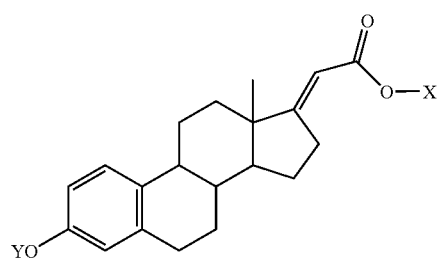

(IX)

wherein X and Y are independently lower alkyl, with an alkali metal in the presence of ammonia or an alkylamine.

Figure 8:
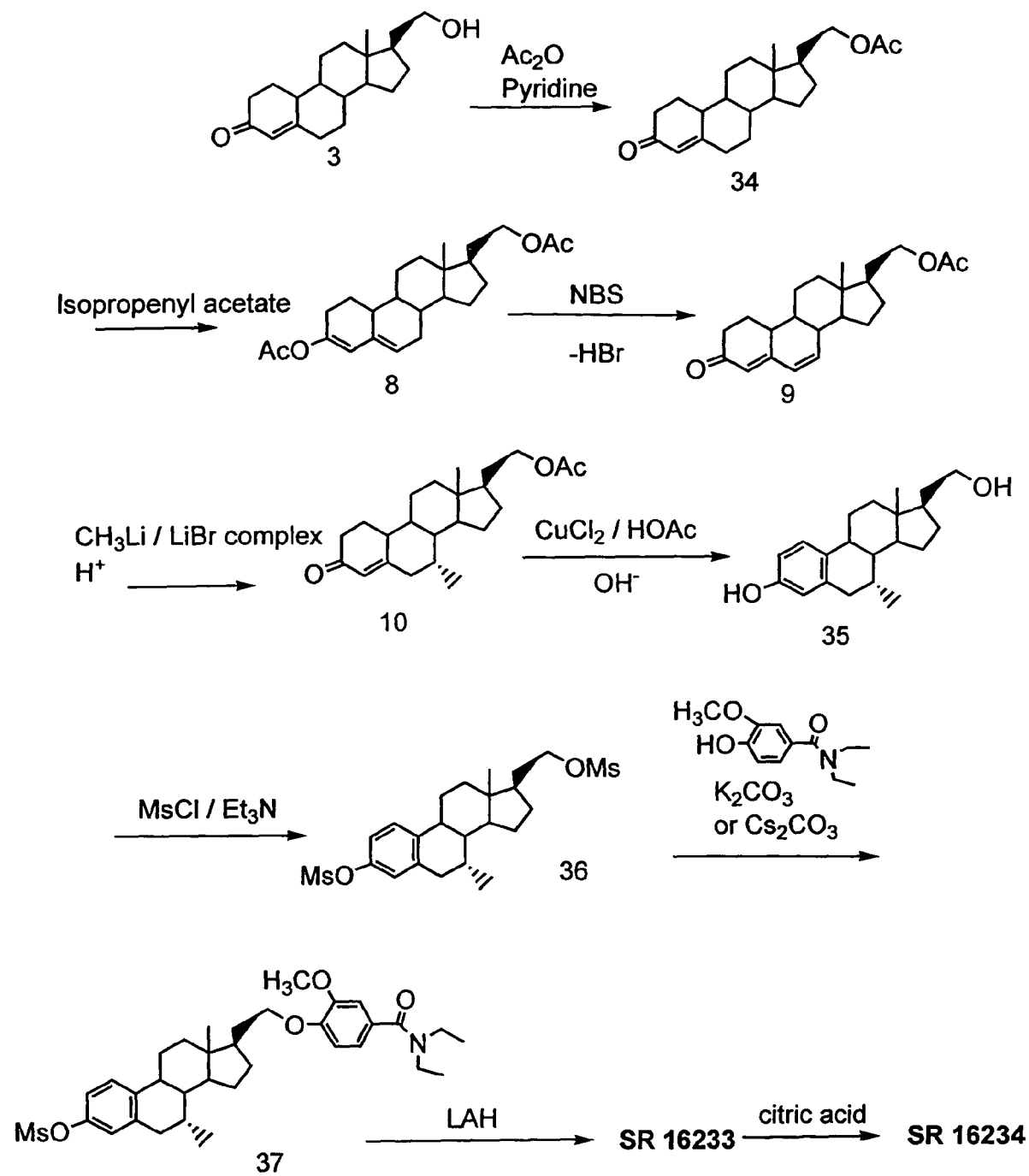
FIGS. 8 and 9 are schemes illustrating methods of the invention for synthesizing SR 16234 from a crude 21-hydroxy-19-norpregna-4-en-3-one (3a).

SR 16234 or its free base SR 16233 is synthesized from compound (III) using one of several methods, exemplified in the schemes of FIGS. 2, 3, 4, 8, and 9. In the first three of these methods, when $R^{19}$ is hydroxyl or hydroxymethyl, preferably hydroxymethyl, the alcohol moiety is initially converted to a leaving group displaceable with an incoming nucleophile as explained above. The remaining steps in the first three methods then differ, as illustrated in FIGS. 2, 3, and 4. In the fourth method, as illustrated in the scheme of FIG. 8, the $R^{19}$ alcohol moiety is initially converted to a protecting group, as explained above, a 7α groups is attached to the B ring, the $R^{19}$ protected group is unprotected and then activated with a leaving group. The fifth method, illustrated in FIG. 9, first protects the $R^{19}$ position and then proceeds as indicated.

In methods 1 and 2 (illustrated in FIGS. 2 and 3), a compound having the structural formula (XII)

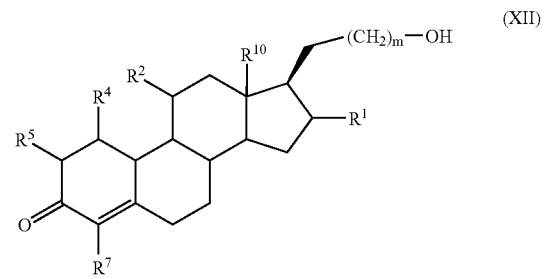

(XII)

wherein m is zero or 1, and $R^1$, $R^2$, $R^4$, $R^5$, $R^7$, and $R^{10}$ are as defined above, is initially provided. This compound is a subset of formula III. The —OH group at the 20- or 21-position (depending on whether m is zero or 1, respectively) is then activated by conversion to an —O—LG moiety wherein LG is a leaving group displaceable by nucleophilic attack, as explained above; LG can be, for example, OMs, OTs, Cl, Br, etc.

At the same time that the —OH group at the 20- or 21-position is activated, or subsequently, the following three reaction steps are carried out: (1) the A ring of the steroid nucleus is oxidized (aromatized); (2) a 6-keto moiety is provided by exposure to gaseous oxygen in the presence of base (e.g., cesium carbonate or potassium acetate); and (3) a protecting group is introduced at the 3-position so as to provide a protected hydroxyl group —OPr wherein Pr is the protecting group. Suitable protecting groups include, but are not limited to alkyl, lower alkyl, Ms, Ts, Ac, and THP.

Next, the leaving group LG is displaced with a hydroxyl-containing compound having the structural formula (XIII)

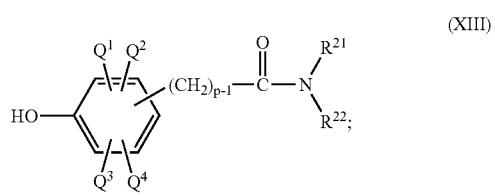

(XIII)

wherein p is an integer in the range of 1 to 7 inclusive, $R^{21}$ and $R^{22}$ are lower alkyl or are linked together to form a five- or six-membered heterocycloalkyl ring, and $Q^1$, $Q^2$, $Q^3$, and $Q^4$ are independently selected from the group consisting of hydrogen, hydroxyl, carboxyl, alkoxy, alkyl, halogen, amino, and alkyl-substituted amino.

Prior, during, or subsequent to the aforementioned reactions, substitution at the 7-position is effected by reaction with an alkyl halide such as methyl iodide, in a suitable base such as lithium diisopropylamide, to provide a 7-lower alkyl, e.g., a 7-methyl, substituent. In method 1, illustrated in FIG. 2, alkylation at the 7-position is conducted prior to attachment of the aromatic side chain at the 17-position, using an alkyl halide such as methyl iodide. In method 2, illustrated in FIG. 3, alkylation at the 7-position is conducted after attachment of the aromatic side chain at the 17-position, again using an alkyl halide such as methyl iodide. In method 3, the 7-position is alkylated earlier, as implied above by the definition of $R^3$ in structure (III). In either method 1 or 2, the compound provided (exemplified as 6 in FIGS. 2 and 3) can be generically represented as (XVIII)

In method 3, illustrated in FIG. 4, the reaction steps following synthesis of compound (III) (exemplified as 3 in the figure) differ from the foregoing syntheses, as follows. Following protection of the hydroxyl or hydroxymethyl group at $R^{19}$, the 7α-lower alkyl, e.g., 7α-methyl, group is synthesized by reaction with, for example, alkyl lithium, e.g., methyl lithium, in the presence of lithium bromide (see FIG. 4). The hydroxyl or hydroxymethyl group at $R^{19}$ is then deprotected by treatment with base (e.g., an inorganic hydroxide such as KOH or NaOH, in alcohol) using conventional means, followed by reaction with an aldehyde that may be generically represented as (XIV)

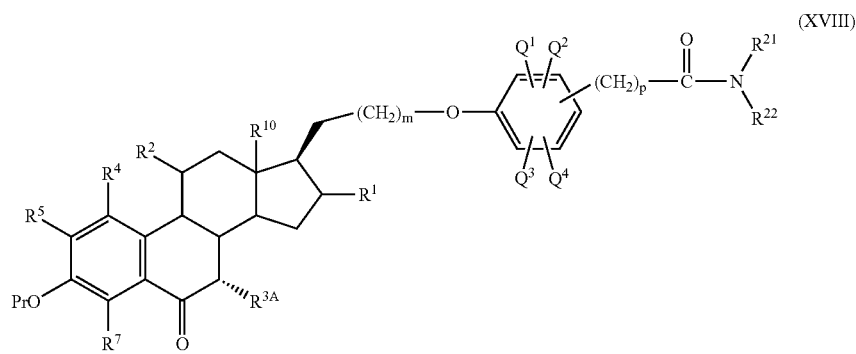

(XVIII)

wherein $R^{3A}$ represents the newly added lower alkyl group and the remaining substituents are as defined previously. It will be appreciated that other types of hydrocarbyl groups could be added at the 7-position, i.e., as $R^{3A}$, by reaction with the appropriate hydrocarbyl halide reagents.

Compound (XVIII) is then reduced so as to remove the 6-keto and amidocarbonyl moieties using a standard reducing agent and conditions, e.g., lithium aluminum hydride (LAH) in the presence of aluminum chloride (AlCl$_3$), which also deprotects at the 3-position to result in a free hydroxyl group. The resulting compound thus has the structure (XI)

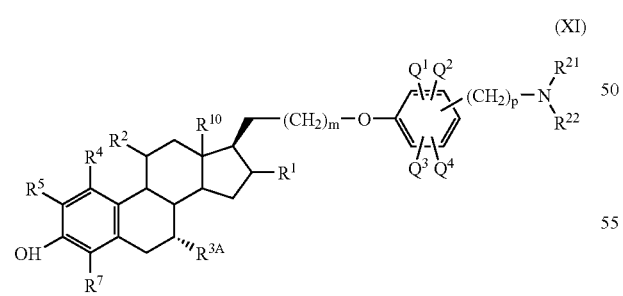

(XI)

A representative compound of structure (XI) compound and key species is 3-hydroxy-7α-methyl-21-[2'-methoxy-4'-(diethylaminomethyl)-phenoxy]-19-norpregna-1,3,5(10) triene (SR 16233) as illustrated in FIGS. 2 and 3. Compound (XI) may then be converted to an acid addition salt by reaction with a suitable acid using conventional procedures. For example, to convert the compound to SR 16234, the citrate salt of SR 16233, the reaction is conducted with citric acid.

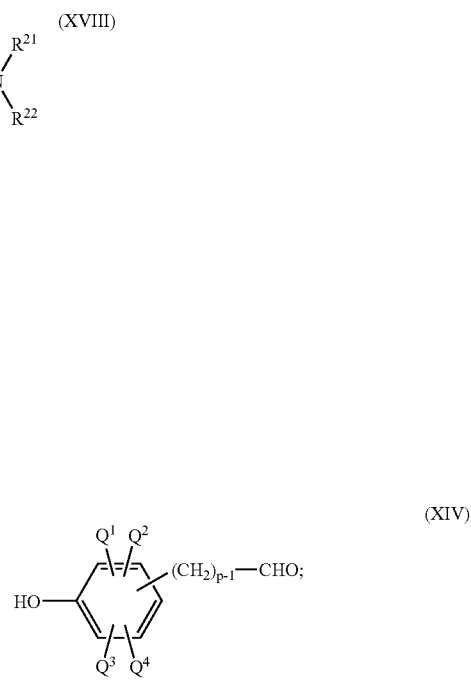

(XIV)

a specific example of such an aldehyde, as illustrated in FIG. 4, is vanillin, i.e., 4-hydroxy-3-methoxybenzaldehyde. This results in an intermediate having the structural formula (XV)

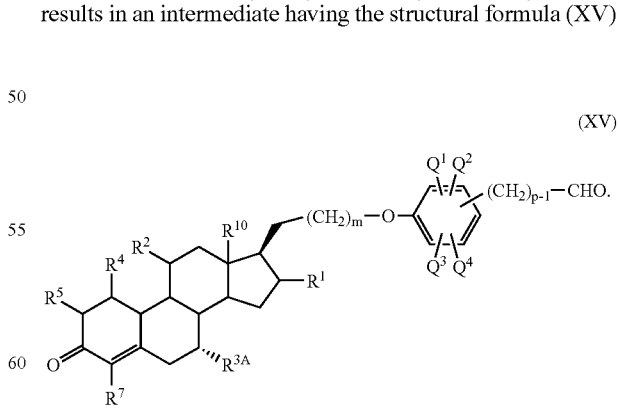

(XV)

Then, in order to provide the desired amine, (XV) is treated with an alkylamine having the structure HNR$^{21}$R$^{22}$ under reaction conditions effective to produce the amine (XVI)

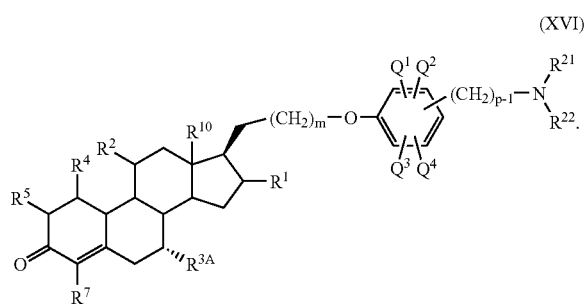

(XVI)

While compound (XVI) is a valuable intermediate in the ultimate synthesis of SR 16234 and analogs thereof, it has additional value as a therapeutic agent, particularly in the treatment of prostate disorders such as prostatic cancer. Preferred compounds within this group have the structural formula (XVII)

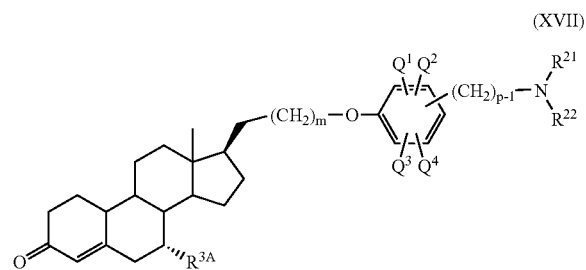

(XVII)

wherein:

$R^{3A}$ is alkyl, most preferably lower alkyl such as methyl;

m is zero or 1;

p is an integer in the range of 1 to 7 inclusive;

$R^{21}$ and $R^{22}$ are lower alkyl or are linked together to form a five- or six-membered heterocycloalkyl ring; and $Q^1$, $Q^2$, $Q^3$, and $Q^4$ are independently selected from the group consisting of hydrogen, hydroxyl, carboxyl, alkoxy, alkyl, halogen, amino, and alkyl-substituted amino.

In method 3, the A ring is then oxidized (aromatized) using, for example, cuprous chloride in AcOH, or by using biological aromatization. SR 16233 results, which can be converted to SR 16234, as noted previously, by reaction with citric acid.

In method 4, as illustrated in FIG. 8, a compound having the structural formula (XII) is used as the starting material. The —OH group at the 20- or 21-position (depending on whether m is zero or 1, respectively) is first protected by conversion to an —O—Pr moiety wherein Pr is a protecting group, as explained above. Suitable protecting groups include, but are not limited to alkyl, lower alkyl, Ms, Ts, Ac, and THP. As illustrated in FIG. 8, acetyl is a preferred protecting group for this purpose, as the acetate moiety allows for easy and efficient purification of the resultant acetate via recrystallization.

Next, a dienyl acetate having structural formula (XX) is formed by introduction of a protecting group, $Pr^2$, at the 3-position.

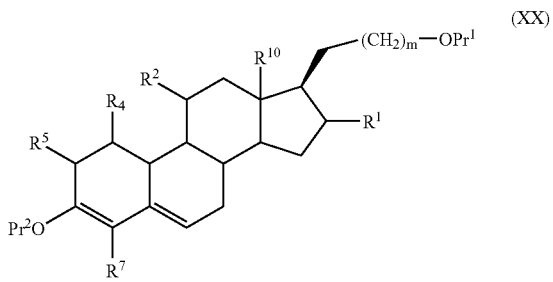

(XX)

In structural formula (XX), m, $R^1$, $R^2$, $R^4$, $R^5$, $R^7$, and $R^{10}$ are as defined above, and $Pr^1$ and $Pr^2$ are the respective protecting groups on the 20- or 21- and the 3-position and may be the same or different. As discussed above, preferred protecting groups include, but are not limited to, alkyl (particularly lower alkyl), acetyl, Ms, Ts, and THP. The 3-position protecting group, $Pr^2$, is then removed to form a dienone having structural formula (XXI)

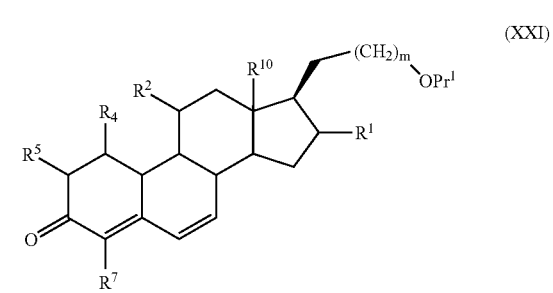

(XXI)

wherein $Pr^1$, m, $R^1$, $R^2$, $R^4$, $R^5$, $R^7$, and $R^{10}$ are as defined above. Once the dienone has been synthesized, the compound is reacted with, for example, a lower alkyl lithium, e.g., methyl lithium, in the presence of lithium bromide to form a 7α-alkylated compound having the structure (XXII)

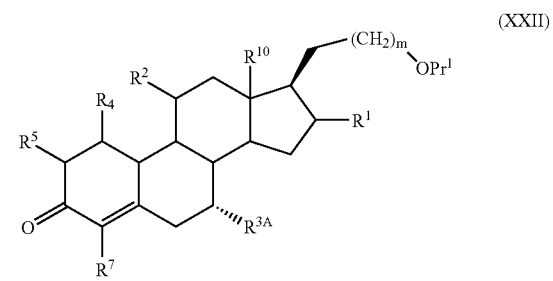

(XXII)

wherein $R^{3A}$ represents the newly added lower alkyl group and the remaining substituents are as defined above (see FIG. 8). The use of acetate as the $Pr^1$ protecting group greatly facilitates the addition of the 7-alkyl group in the a position. While not wishing to be limited by theory, it is believed that the acetate moiety forms a complex with the lithium and promotes introduction of the 7-alkyl functionality from the a face of the steroid.

The A ring of the 7α-alkyl steroid is then aromatized and the $Pr^1$ protecting group removed using, for example, cuprous chloride in AcOH, biological aromatization, or the like.

The resulting diol will have structural formula (XIII)

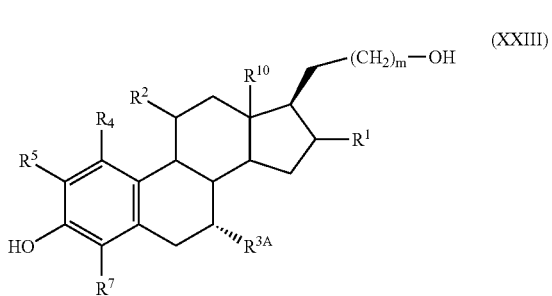

(XXIII)

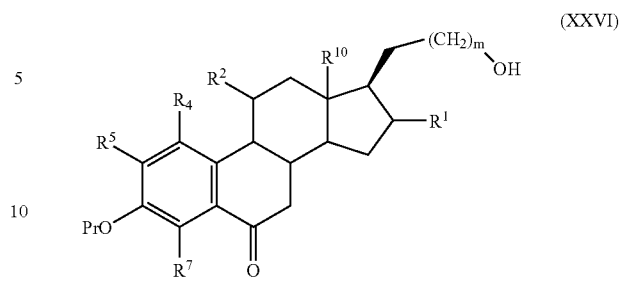

(XXVI)

wherein the various substituents are as defined above. The 3-position and 20- or 21-position alcohol moieties of the diol are then protected with a suitable protecting group such as Ts, Ms, or the like. As discussed above, Ms is a preferred protecting group. The protected compound is then treated with a hydroxyl-containing compound having structural formula (XIII), as discussed above with respect to method 1, resulting in a compound having the structure (XXIV)

wherein Pr, m, $R^1$, $R^2$, $R^4$, $R^5$, $R^7$, and $R^{10}$ are as defined above. The 20- or 21-position hydroxyl group, depending on m, is then protected, e.g., as a THP ether. Once the 20- or 21-position protecting group is in place, substitution is effected at the 7-position by reaction with a lower alkyl halide such as methyl iodide, in a suitable base such as lithium diisopropylamide, to provide a 7α-alkyl, e.g., a 7α-methyl, substituent and remove the 20- or 21-position protecting group. After the 7α-alkyl group is in place, the 6-ketone is

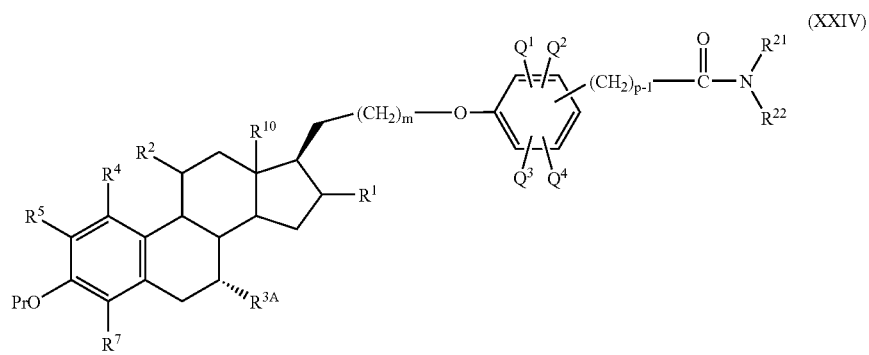

(XXIV)

wherein Pr represents the protecting group on the 3-position and the remaining substituents are as defined previously. This compound is then reduced using a standard reducing agent and conditions, e.g., lithium aluminum hydride (LAH), to reduce the amido moiety to an amine and deprotect at the 3-position resulting in a free hydroxyl group. The resulting compound thus has the structure (XI), which, as previously discussed, may then be converted to an acid addition salt by reaction with a suitable acid using conventional procedures.

Figure 9:
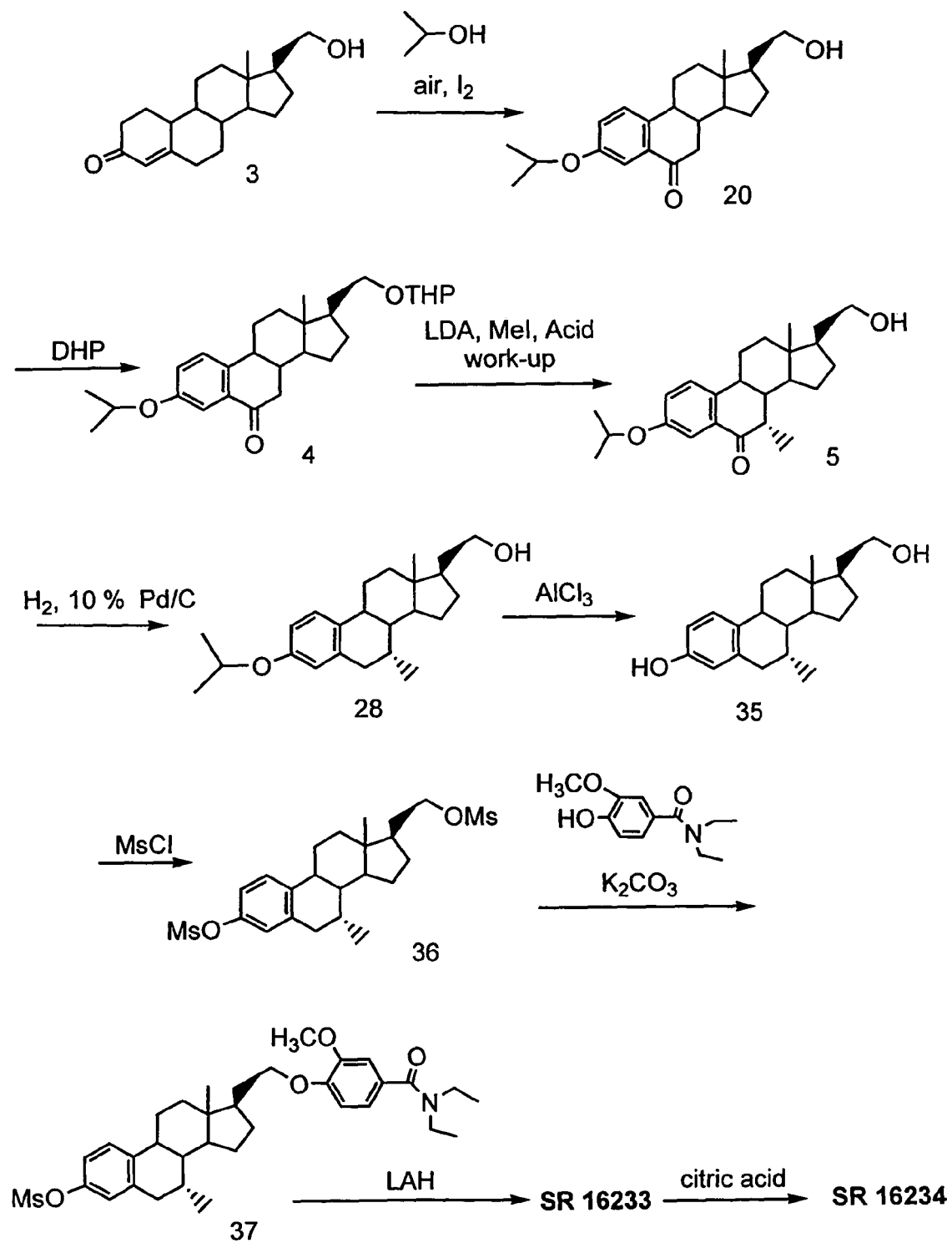

In the last method, method 5, illustrated in FIG. 9, the 3-position of a compound having the structural formula (XII) is protected, the A ring aromatized and the desired 6-ketone introduced by the use of a catalytic amount of iodine in isopropanol while air is bubbled through the reaction mixture. This process results in a 6-ketone having the structural formula (XXVI)

catalytically removed using hydrogen and a platinum or palladium catalyst, e.g., 10% palladium on carbon, and the 3-position is deprotected with a suitable reagent to provide an alcohol, resulting in the diol having the structure (XXIII). The remainder of the method then proceeds as described for method 4.

Surprisingly, it has been discovered that a THP ether protecting group when used in conjunction with an alkyl halide and a base, allows for a highly stereoselective addition of a 7-alkyl group in the α position on standard 6-keto steroid compounds. While not wishing to be limited by theory, it is believed that the THP moiety sterically hinders addition of the 7-alkyl functionality from the β face of the steroid, thereby promoting introduction of the 7-alkyl functionality from the a face of the steroid. The use of a THP ether in the 7α-methylation of 6-keto estradiol is described in Example 8.

Additional Intermediates:

Additional compounds within the scope of the invention are useful as intermediates in one or more of the foregoing syntheses and have the structural formula (V)

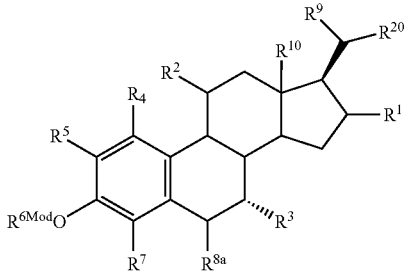
(V)

wherein:

R[1] is hydrogen or CR[11]R[12], wherein R[11] and R[12] are hydrogen or lower alkyl;

R[2] is selected from the group consisting of hydrogen, hydroxyl, alkyl, —OR[13], and —SR[13] wherein R[13] is alkyl;

R[3] is selected from the group consisting of hydrogen and hydrocarbyl, preferably hydrogen and alkyl, e.g., lower alkyl such as methyl;

R[4], R[5], and R[7] are independently selected from the group consisting of hydrogen and lower alkyl;

R[6Mod] is selected from the group consisting of hydrogen, alkyl, acyl, —C(O)-aryl, and —C(O)-alkyl, hydroxyl-protecting groups, and hydroxyl-activating groups;

R[8a] is selected from the group consisting of hydrogen, hydroxyl, oxo, and —OR[18] wherein R[18] is lower alkyl or lower acyl;

R[9] is hydrogen or alkyl;

R[10] is methyl or ethyl; and

R[20] is hydroxyl, hydroxymethyl, protected hydroxyl, protected hydroxymethyl, activated hydroxyl, activated hydroxymethyl, or

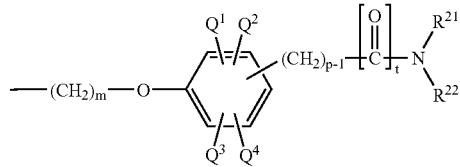

in which m is zero or 1, p is an integer in the range of 1 to 7 inclusive, and t is zero or 1, with the proviso that when R[8a] is oxo, t is 1, and R[21] and R[22] are lower alkyl or are linked together to form a five- or six-membered heterocycloalkyl ring; and Q[1], Q[2], Q[3], and Q[4] are independently selected from the group consisting of hydrogen, hydroxyl, carboxyl, alkoxy, alkyl, halogen, amino, and alkyl-substituted amino.

Preferred compounds within this group have the structure of formula (VI)

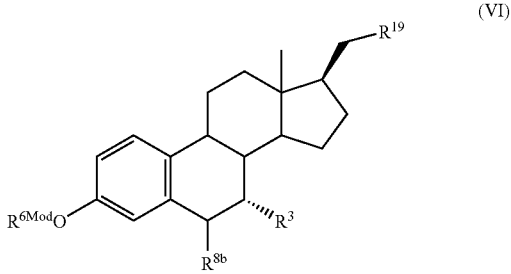
(VI)

wherein:

R[3] is hydrogen or lower alkyl;

R[6Mod] is hydrogen or a hydroxyl-protecting group;

R[8b] is hydrogen, hydroxy, or oxo; and

R[19] is hydroxyl, hydroxymethyl, protected hydroxyl, or protected hydroxymethyl. In particularly preferred compounds, R[19] is hydroxylmethyl.

Other novel compounds useful as intermediates herein have the general structure (VII)

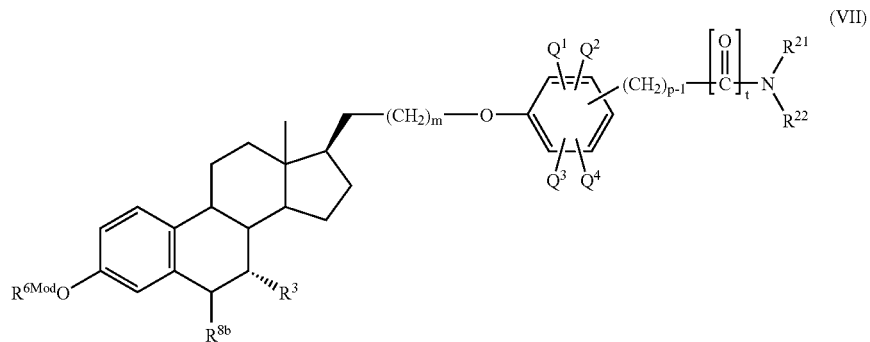
(VII)

wherein:

$R^3$ is hydrogen or hydrocarbyl, preferably hydrogen or alkyl, most preferably hydrogen or lower alkyl such as methyl;

$R^{6Mod}$ is selected from the group consisting of hydrogen, alkyl, acyl, —C(O)-aryl, and —C(O)-alkyl, hydroxyl-protecting groups, and hydroxyl-activating groups;

$R^{8b}$ is hydrogen, hydroxyl, or oxo, but preferably is hydrogen or oxo;

m is zero or 1;

p is an integer in the range of 1 to 7 inclusive;

t is zero or 1, with the proviso that when $R^{8a}$ is hydrogen, t is zero, and when $R^{8a}$ is oxo, t is 1;

$R^{21}$ and $R^{22}$ are lower alkyl or are linked together to form a five- or six-membered heterocycloalkyl ring; and $Q^1$, $Q^2$, $Q^3$, and $Q^4$ are independently selected from the group consisting of hydrogen, hydroxyl, carboxyl, alkoxy, alkyl, halogen, amino, and alkyl-substituted amino.

Still other compounds useful as intermediates herein have the general structure (VIII)

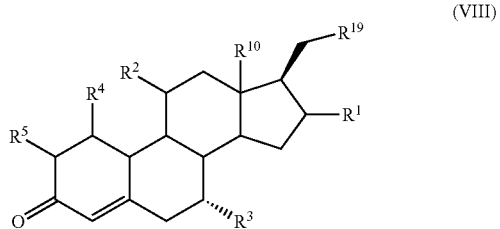

wherein $R^1$, $R^2$, $R^3$, $R^4$, $R^5$, $R^{10}$, and $R^{19}$ are as defined previously.

Also useful are compounds having the structure (XXVII) and (XXVIII)

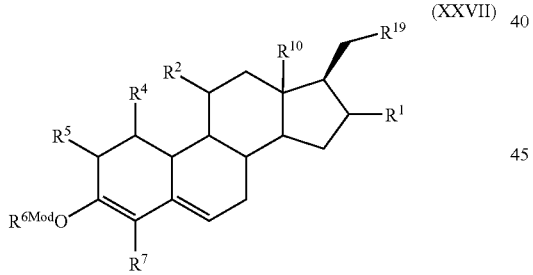

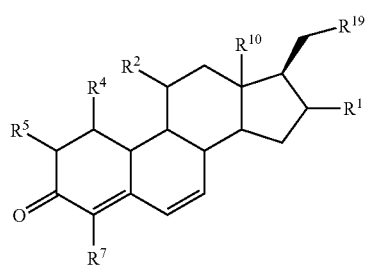

wherein $R^1$, $R^2$, $R^4$, $R^5$, $R^{6Mod}$, $R^7$, $R^{10}$, and $R^{19}$ are as defined previously.

Pharmaceutical Utility:

A number of those compounds identified herein as synthetic intermediates also find utility as pharmaceutical agents. For example, as alluded to in the preceding section, certain compounds useful as intermediates in the synthetic methods described in the preceding section are also useful in the treatment of prostate disorders, particularly prostatic cancer.

Prostatic cancer is the second most common malignancy in American men. Prostatic cancer may produce symptoms of urethral obstruction, either by direct extension into the bladder or by spreading behind the bladder through-the seminal vesicles. Like-benign prostatic hyperplasia, prostatic cancer increases in prevalence with patient age, requires androgens for growth and development, and responds to antiandrogen treatment. Bostwick, et al., *Cancer*, 70(1 Suppl): 291-301 (1992). Prostatic cancer has been treated medically with some success through surgical techniques such as radical prostatectomy, and through radiation therapy via either external beam or surgical implants of interstitial radioactive seeds into the prostate. Hormonal therapies available include ablation by castration, administration of exogenous estrogens to deprive prostatic tumors of circulating androgens, releasing hormone analogues that inhibit testosterone synthesis, and/or administering antiandrogens which block androgen action in the prostate itself. Chemotherapy has yielded discouraging results. See, e.g., *Cecil Textbook of Medicine*, 19th ed, 1353 (Wyngaarden et al., eds., W. B. Saunders 1992).

Although a number of therapies have been proposed to treat each of these disorders, there remains a need in the art to provide a more effective method of treating prostatic disorders such as prostatic cancer. It is, thus, a significant discovery that certain compounds of the invention are useful in the treatment of prostatic cancer.

One group of compounds that may be used to treat prostatic cancer has the structural formula (XVI).

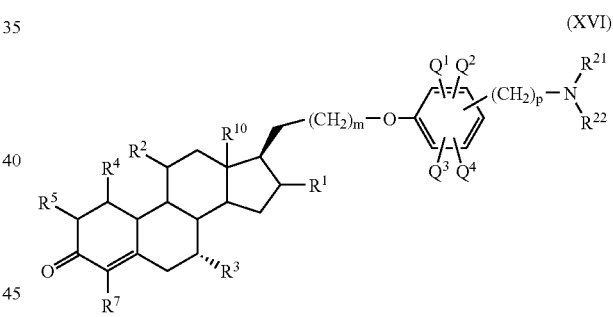

In compound (XVI), the various-substituents are as follows:

$R^1$ is $CR^{11}R^{12}$, wherein $R^{11}$ and $R^{12}$ are hydrogen or lower alkyl;

$R^2$ is selected from the group consisting of hydrogen, hydroxyl, alkyl, —$OR^{13}$, and —$SR^{13}$ wherein $R^{13}$ is alkyl;

$R^3$ *is* hydrogen or hydrocarbyl, preferably hydrogen or alkyl, more preferably hydrogen or lower alkyl such as methyl;

$R^4$ and $R^5$ are independently selected from the group consisting of hydrogen and lower alkyl;

$R^7$ is hydrogen or lower alkyl;

$R^{10}$ is methyl or ethyl;

m is zero or 1;

p is an integer in the range of 1 to 7 inclusive;

$R^{21}$ and $R^{22}$ are lower alkyl or are linked together to form a five- or six-membered heterocycloalkyl ring; and $Q^1$, $Q^2$, $Q^3$, and $Q^4$ are independently selected from the group consisting of hydrogen, hydroxyl, carboxyl, alkoxy, alkyl, halogen, amino, and alkyl-substituted amino.

The compound may also be in the form of a pharmacologically acceptable acid addition salt.

Preferred compounds within the generic structure of formula (XVI) have the structural formula (XVII)

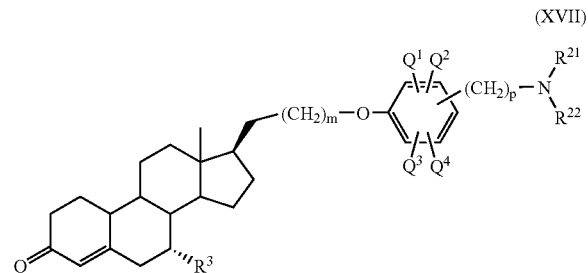
(XVII)

wherein:

$R^3$, m, p, $R^{21}$, $R^{22}$, $Q^1$, $Q^2$, $Q^3$, and $Q^4$ are as defined above for formula (XVI).

Two exemplary such compounds are as follows:

COMPOUND 13, FIG. 4:

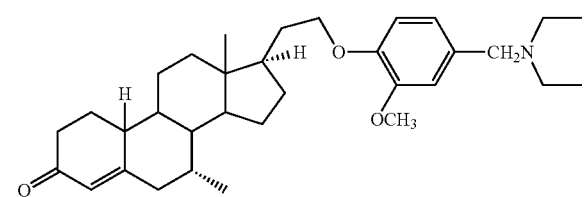

COMPOUND SR 16312:

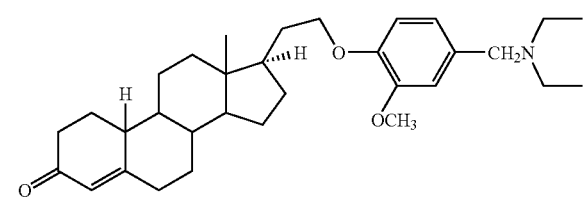

The compounds may be in the form of pharmacologically acceptable salts, prodrugs, or other derivatives or analogs, or they may be modified by appending one or more appropriate functionalities to enhance selected biological properties. Such modifications are known in the art and include those which increase biological penetration into a given biological system, increase oral bioavailability, increase solubility to allow administration by injection, and the like.

Acid addition salts of the free amine compounds can be prepared using standard procedures known to those skilled in the art of synthetic organic chemistry and described, for example, by J. March, *Advanced Organic Chemistry: Reactions, Mechanisms and Structure*, 4th Ed. (N.Y.: Wiley-Interscience, 1992); conventional preparation of an acid addition salt involves reaction of the free base with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid,.p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preferred acid addition salts of the present compounds are the citrate, fumarate, succinate, benzoate, and malonate salts.

The therapeutic agents may be conveniently formulated into pharmaceutical compositions composed of one or more of the compounds in association with a pharmaceutically acceptable carrier. See *Remington: The Science and Practice of Pharmacy,* 19th Ed. (Easton, Pa.: Mack Publishing Co., 1995), which discloses typical carriers and conventional methods of preparing pharmaceutical compositions which may be used as described or modified to prepare pharmaceutical formulations containing the compounds of the invention. The compounds may also be administered in the form of pharmaceutically acceptable salts, or as pharmaceutically acceptable esters, as described in the preceding section.

The compounds may be administered orally, parenterally, transdermally, rectally, nasally, buccally, or via an implanted reservoir in dosage formulations containing conventional non-toxic pharmaceutically acceptable carriers, adjuvants, and vehicles. The term "parenteral" as used herein is intended to include subcutaneous, intravenous, and intramuscular injection. The amount of active compound administered will, of course, be dependent on the subject being treated, the subject's weight, the manner of administration, and the judgment of the prescribing physician. Generally, however, dosage will be in the range of approximately 0.01 mg/kg/day to 10.0 mg/kg/day, more preferably in the range of about 1.0 mg/kg/day to 5.0 mg/kg/day.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

For oral administration, the composition will generally take the form of a tablet or capsule, or may be an aqueous or nonaqueous solution, suspension, or syrup. Tablets and capsules are preferred oral administration forms. Tablets and capsules for oral use will generally include one or more commonly used carriers such as lactose and cornstarch. Lubricating agents, such as magnesium stearate, are also typically added. When liquid suspensions are used, the active agent is combined with emulsifying and suspending agents. If desired, flavoring, coloring, and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium.

The compounds of the invention may also be administered through the skin or mucosal tissue using conventional transdermal drug delivery systems, wherein the agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

Alternatively, the pharmaceutical compositions of the invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax, and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Formulations for buccal administration include tablets,- lozenges, gels-and the like. Alternatively, buccal administration can be effected using a transmucosal delivery system.

It is to be understood that while the invention has been described in conjunction with the preferred specific embodiments thereof, the foregoing description as well as the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entirety.

EXPERIMENTAL

The practice of the present invention will employ, unless otherwise indicated, conventional techniques of synthetic organic chemistry, biological testing, and the like, which are within the skill of the art. Such techniques are explained fully in the literature. See, e.g., Fieser et al., *Steroids* (N.Y.: Reinhold, 1959), Djerassi, *Steroid Reactions: An Outline for Organic Chemists* (San Francisco: Holden-Day, 1963), and Fried et al., *Organic Reactions in Steroid Chemistry* vols. 1 and 2 (N.Y.: Reinhold, 1972), for detailed information concerning steroid-related synthetic procedures. Reference may be had to Littlefield et al., *Endocrinology* 127: 2757-2762 (1990) and Wakeling et al., *Endocrinology* 99: 447-453 (1983) for a description of the biological testing procedures useful to evaluate compounds such as some of the therapeutic agents described and claimed herein.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric. All solvents were purchased as HPLC grade, and all reactions were routinely conducted under an inert atmosphere of argon unless otherwise indicated. All reagents were obtained commercially unless otherwise indicated. Estrone 3-methyl ether was purchased from Berlichem U.S.; ethamivan (vanillic acid diethylamide) was obtained from Fluka. NMR analyses were conducted on a Varian Gemini 300 and were referenced to chloroform at $\delta$ 7.27. Mass spectra were recorded on an LKB Model 9000 combination gas chromatograph-mass spectrometer, interfaced with a teknivent Vector-1 Data System.

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for.

EXAMPLE 1

Synthesis of 21-hydroxy-19-norpregna-4-en-3-one (3)

This example describes preparation of 21-hydroxy-19-norpregna-4-en-3-one (3) from estrone-3-methyl ether (1) as illustrated in the schemes of FIGS. 2, 3, and 4.

Figure 10:
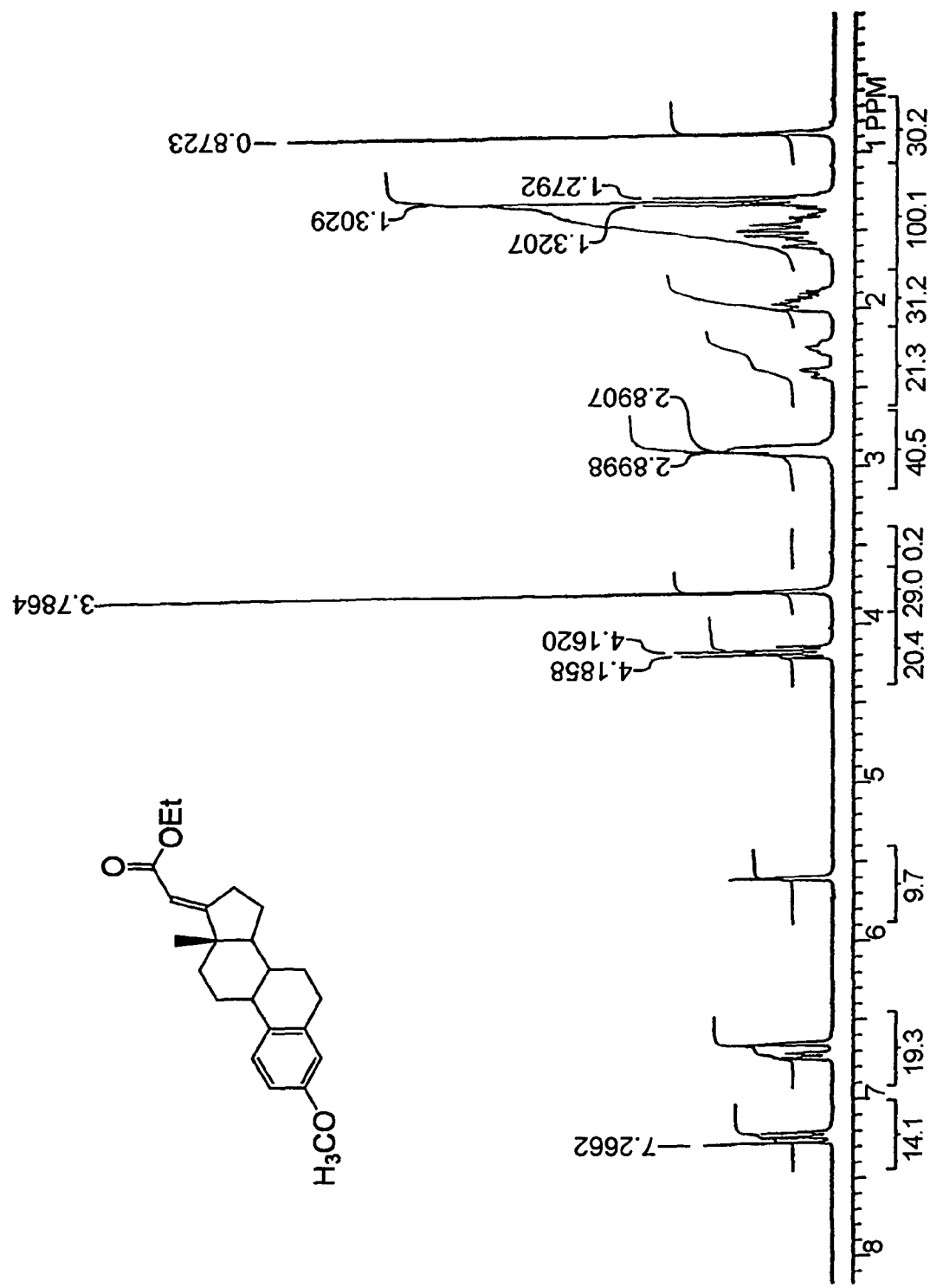
FIG. 10 is a $^1H$ NMR spectrum of compound 2, the structure of which is shown in FIGS. 2, 3 and 4 (synthesized as described in Example 1).

Synthesis of (2): To a mixture of 28.4 g (0.1 mol) of estrone-3-methyl ether (1) and 90 g (0.4 mol) of triethyl phosphonoacetate in 175 mL of THF and 90 mL of ethanol, heated to reflux, was added 130 mL (0.4 mol) of a 21% solution of sodium ethoxide in ethanol. The mixture was refluxed overnight. The mixture was cooled and the volume reduced by half under vacuo. The mixture was poured into 2 L ice water with stirring. A gummy solid precipitated which was filtered, washed with water and with stirring, and air-dried to give 2 as a solid. Yield 34 g (99%). The identity of the product was confirmed using $^1$H NMR spectroscopy, and the NMR spectrum is shown in FIG. 10.

Figure 11:
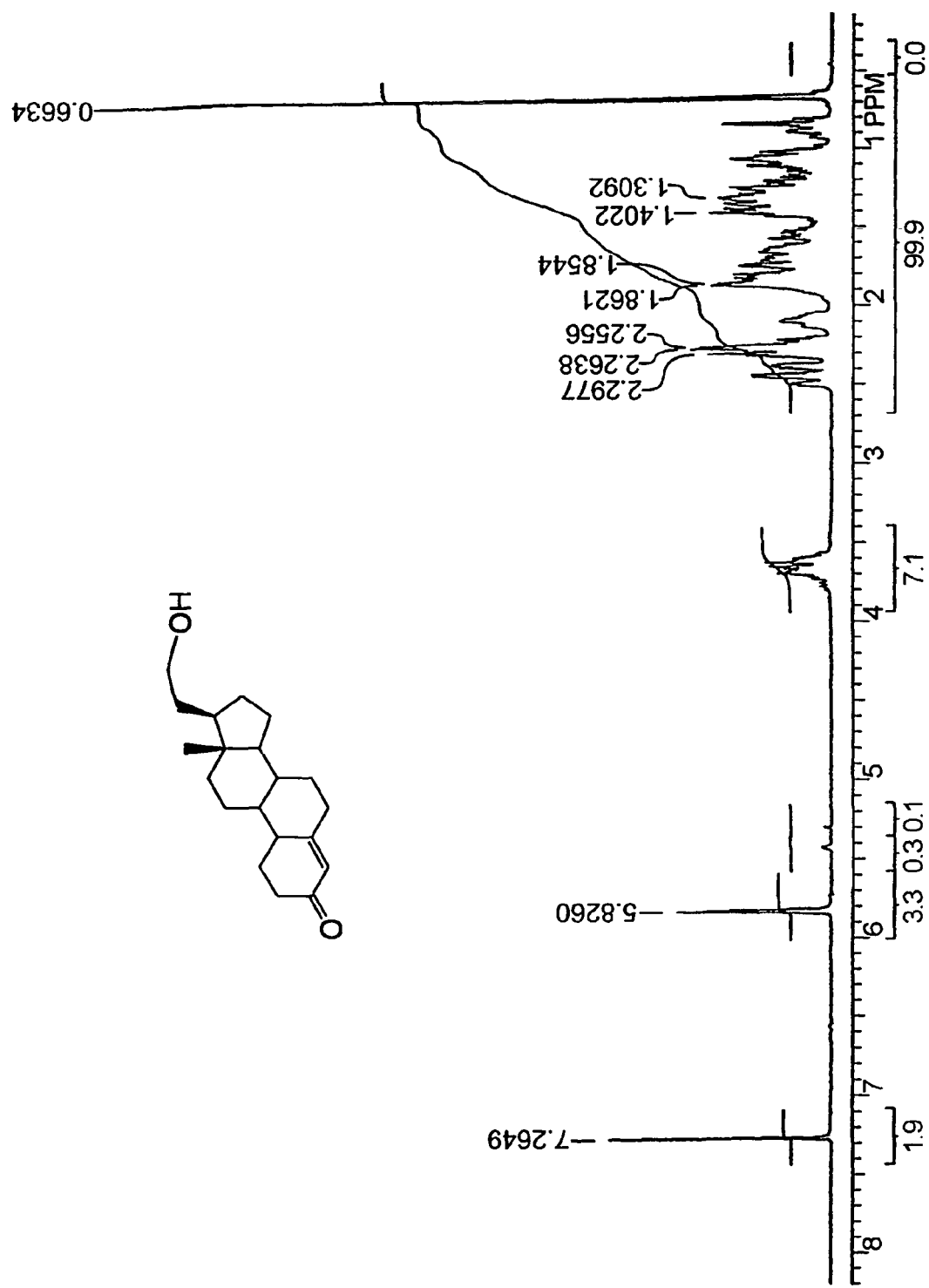
FIG. 11 is a $^1H$ NMR spectrum of compound 3, the structure of which is shown in FIGS. 2, 3 and 4 (synthesized as described in Example 1).

Synthesis of (3): To a three-necked flask equipped with a dry-ice condenser, overhead stirrer, argon gas inlet, and dropping funnel in a dry-ice-acetone bath was added 1200 mL of liquid ammonia. To this −78° C. liquid was added 23.6 (3 mol) g of lithium in 1- to 3-inch pieces. After stirring 15 min, 350 mL of dry THF was slowly added to the blue solution (containing lithium bronze). A solution of 30 g (84.6 mmol) of 2 in 380 mL of t-butanol and 120 mL of THF was slowly added to the blue mixture. After stirring on the dry-ice-acetone bath, 2 g (0.25 moles) more of lithium was added. After stirring for 2 hrs, on the dry-ice-acetone bath, the blue color was mostly gone and a white-solid mixture remained. After three more hrs of stirring, 100 mL of methanol was added and the stirred mixture was allowed to reach room temperature and the ammonia evaporated with a flow of argon overnight. A solution of 140 mL concentrated HCl, 350 mL of water and 500 mL of THF was slowly added to the white semi-solid mixture with overhead stirring. More concentrated HCl was added until pH=1. The solution was stirred at room temperature for 3 hrs. The light yellow solution was poured into 1 L of water and extracted with 4× ethyl ether. The ether was washed with 500 mL of saturated brine, dried over magnesium sulfate, filtered, and evaporated to dryness. Yield 27 g (100%) of a semi-solid crude product 3. After silica gel column chromatography (0-20% ethyl acetate in dichloromethane), 21.8 g (85%) of 3 as a white solid was isolated. The identity of the product was confirmed using $^1$H NMR spectroscopy, and the NMR spectrum is shown in FIG. 11.

EXAMPLE 2

Synthesis of 3-hydroxy-7α-methyl-21-[2'-methoxy-4'-(diethylaminomethyl)-phenoxy]-19-norpregna-1,3,5(10)triene citrate ("SR 16234") from 21-hydroxy-19-norpregna-4-en-3-one, method 1

SR 16234 was synthesized from 21-hydroxy-19-norpregna-4-en-3-one (3) as illustrated in FIG. 2, using the following procedure.

Figure 12:
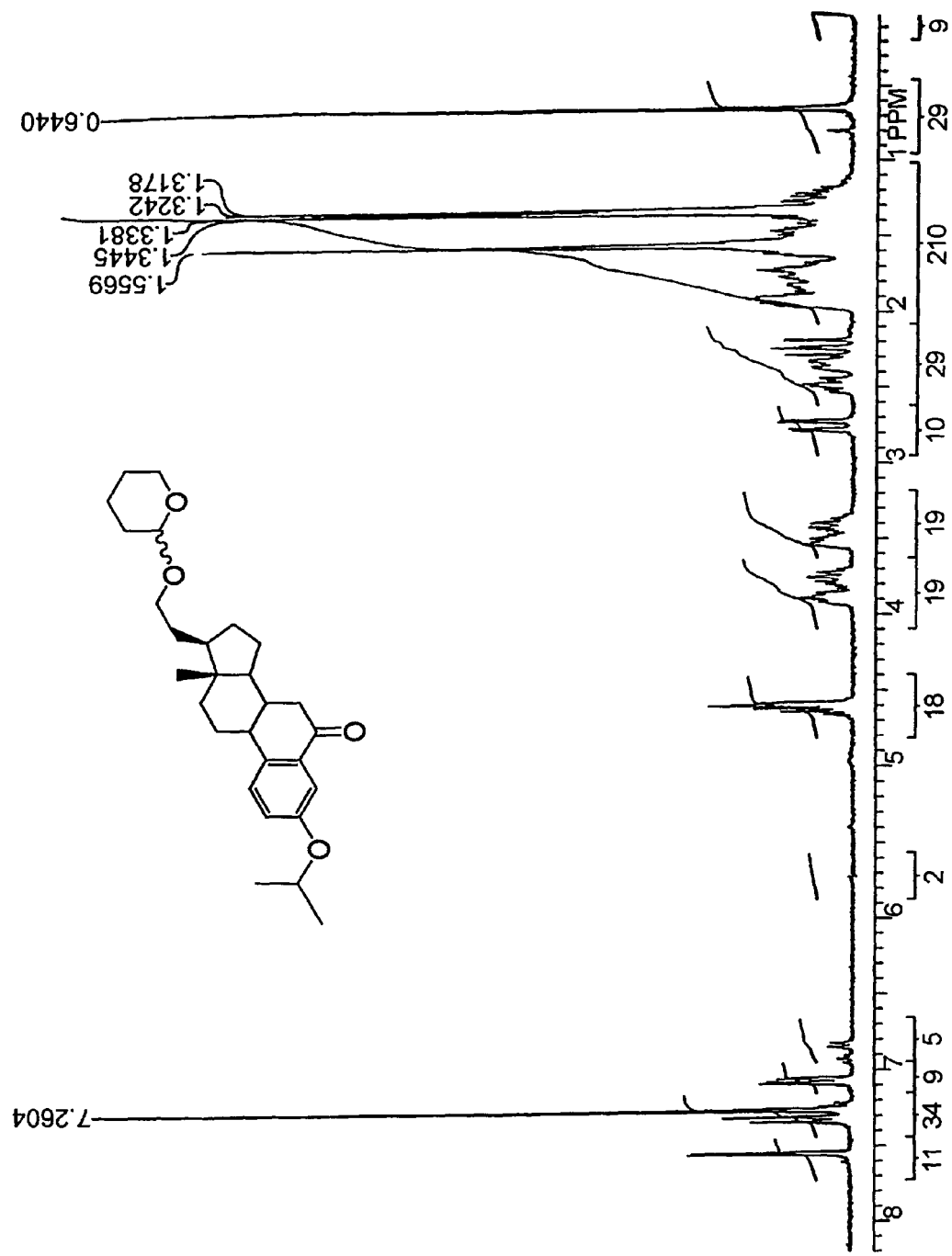
FIG. 12 is a $^1H$ NMR spectrum of compound 4, the structure of which is shown in FIGS. 2 and 3 (synthesized as described in Example 2).

Synthesis of (4): To a solution of 1.32 g (4.36 mmol) of 3 (prepared in Example 1) in 30 mL of $CH_2Cl_2$ was added 2 mL of DHP (dihydropyran). The mixture was cooled to 0° C. and 40 mg (5%) of TsOH was added, and the mixture was stirred for 1.5 h. Triethylamine (0.5 mL) was added to the mixture and the mixture was filtered through a pad of silica gel (ether). The filtrate was concentrated to give 1.79 g of crude product, which was used right away without purification. To this crude product was added 1.23 g (13.1 mmol) of phenol and 4.26 g (13.1 mmol) of $CS_2CO_3$ followed by addition of 30 mL of sulfolane. The resulting mixture was heated at 125-130° C. under a stream of air for 6.5 hrs., and the mixture was cooled to 65° C., and 10.7 mL of isopropyl bromide was added. The mixture was stirred for 2 hrs., and was cooled to ambient temperature, diluted with ether and hexanes (80 mL/120 mL), washed with water (50 mL×4), brine, dried, concentrated, and was chromatographed (10-15% EtOAc in hexanes) to give 735 mg (40%) of 4. The identity of the product was confirmed using $^1$H NMR spectroscopy, and the NMR spectrum is shown in FIG. 12.

Figure 13:
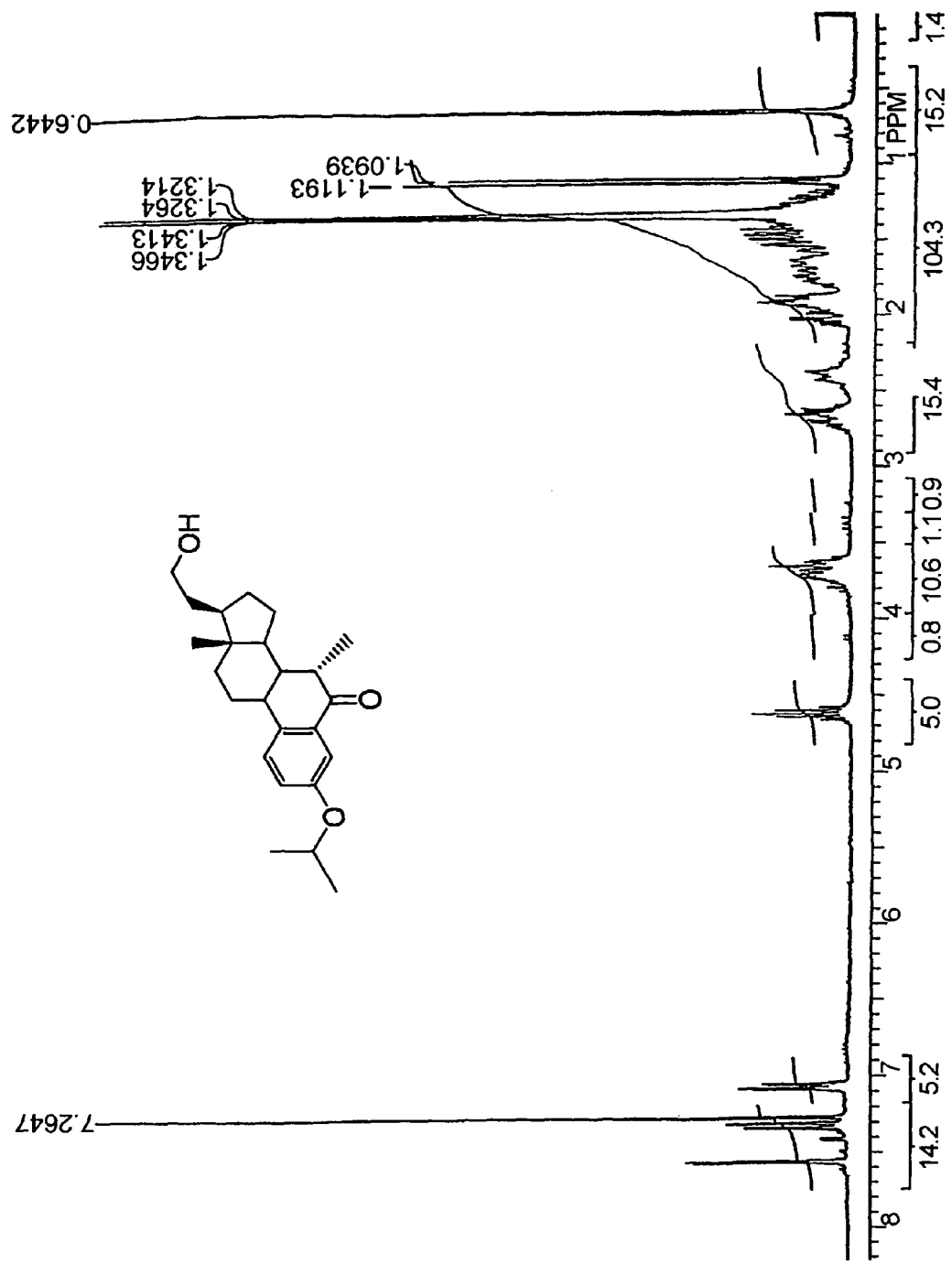
FIG. 13 is a $^1H$ NMR spectrum of compound 5, the structure of which is shown in FIGS. 2 and 3 (synthesized as described in Example 2).

Synthesis of (5): To a solution of 210 mg (0.48 mmol) of 4 in 10 mL of THF was added 1 mL (2 mmol) of a 2.0 M solution of LDA (lithium diisopropylamide) in THF at 0° C. The mixture was stirred for 1 h, warmed to ambient temperature, and was treated with 1 mL of MeI. The resulting mixture was refluxed for 30 min, and was cooled to 0° C. Methanol (10 mL) and TsOH (0.5 g) was added, and was stirred for 1.5 h. Triethylamine (1 mL) was added, and the mixture was concentrated, and was chromatographed (30% EtOAc in hexanes) to give 70 mg (39%) of 5 as an oil. The identity of the product was confirmed using $^1$H NMR spectroscopy, and the NMR spectrum is shown in FIG. 13.

Figure 14:
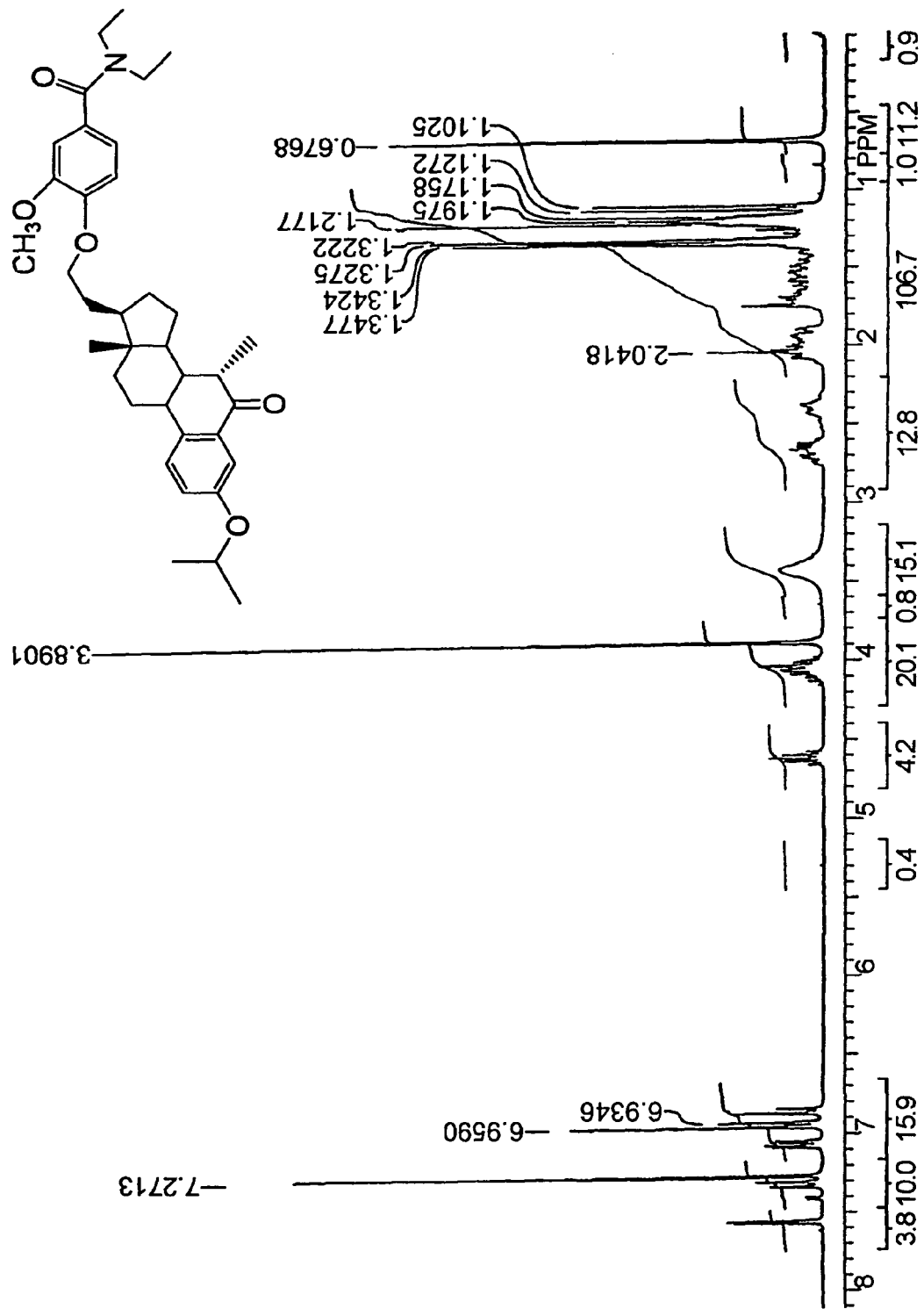
FIG. 14 is a $^1H$ NMR spectrum of compound 6, the structure of which is shown in FIGS. 2 and 3 (synthesized as described in Example 2).

Synthesis of (6): To a solution of 45 mg (0.12 mmol) of 5 and 1 mL of $Et_3N$ in 10 mL of $CH_2Cl_2$ was added 0.5 mL of methanesulfonic anhydride at 0° C. The mixture was stirred for 20 min, and then filtered through a pad of silica gel (ether). The filtrate was concentrated to give an oil, which was dissolved in 5 mL of DMF, and 67 mg (0.28 mmol) of vanillic acid diethylamide and 97 mg (0.30 mmol) of $Cs_2CO_3$ was added. The resulting mixture was heated at 110° C. for 3 h, and was cooled and diluted with ether (75 mL). The mixture was washed with water, brine, dried, concentrated, and was chromatographed (50% EtOAc in hexanes) to give 60 mg (85%) of 6. The identity of the product was confirmed using $^1$H NMR spectroscopy, and the NMR spectrum is shown in FIG. 14.

Figure 15:
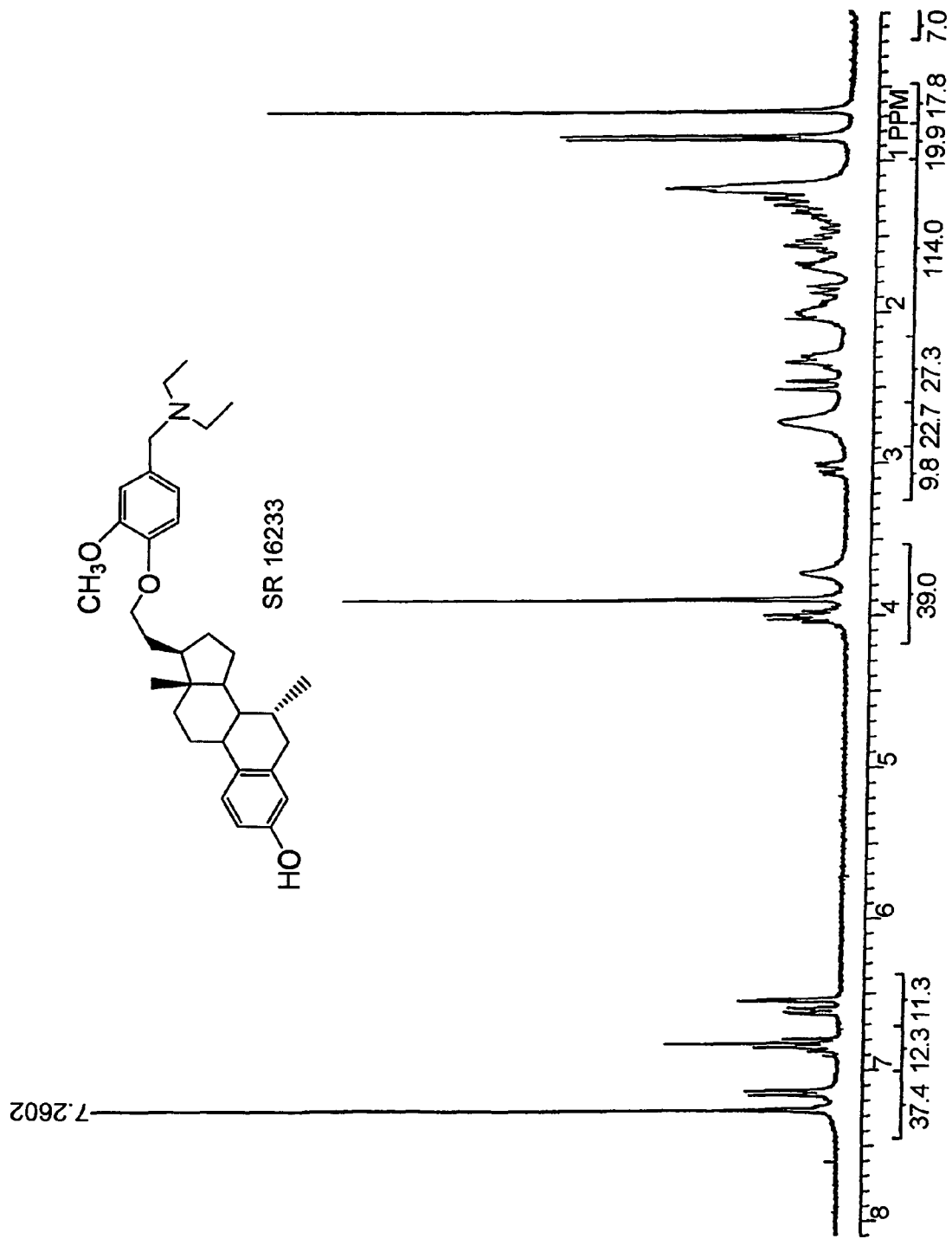
FIG. 15 is a $^1H$ NMR spectrum of compound SR 16233, the structure of which is shown in FIGS. 2 and 3 (synthesized as described in Example 2).
Figure 16:
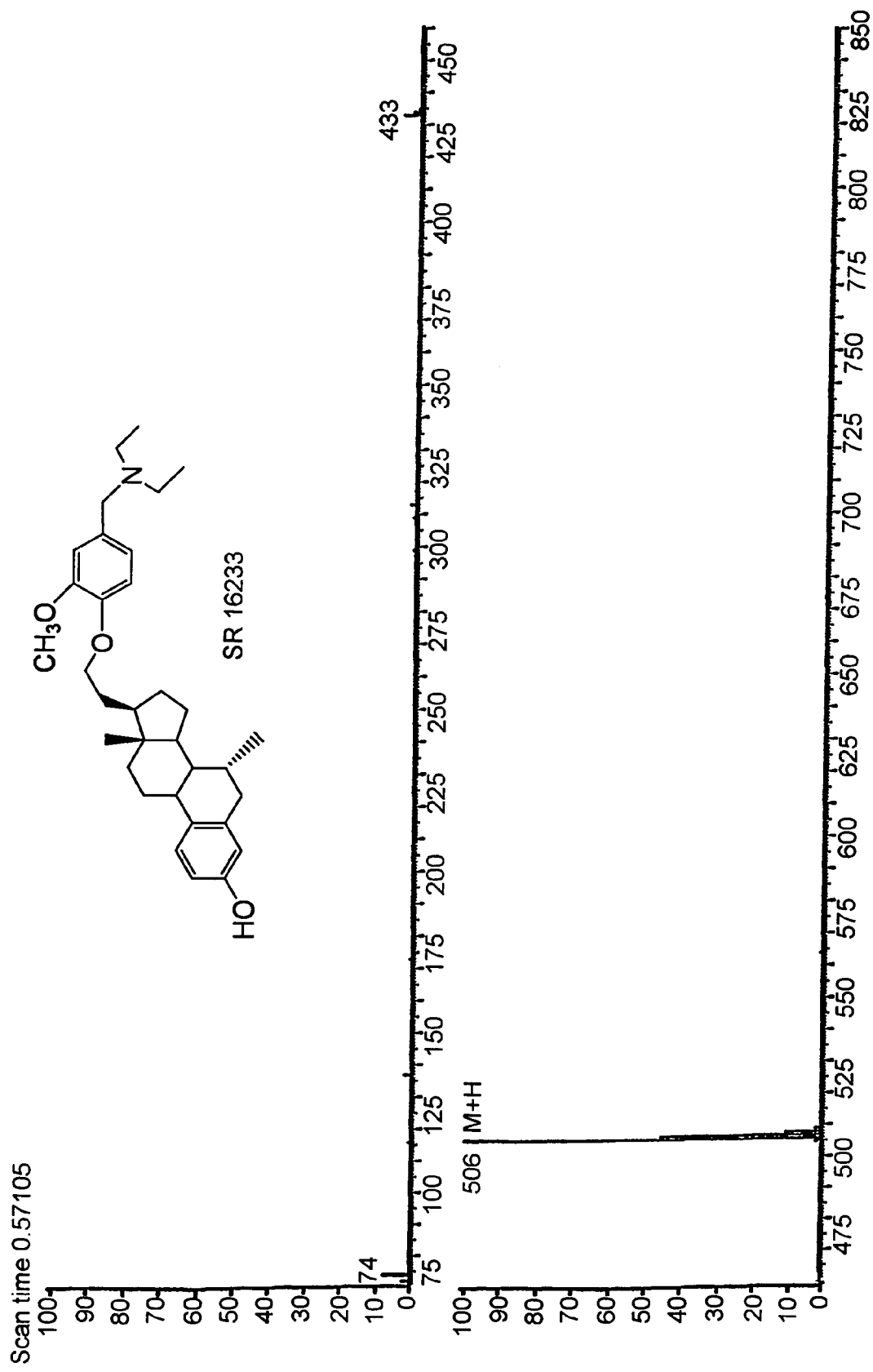
FIG. 16 is a mass spectrum of compound SR 16233.

Synthesis of SR 16233: To a solution of 20 mg (0.03 mmol) of 6 in 5 mL of $CH_2Cl_2$ was added 10 mg (0.07 mmol) of $AlCl_3$ at 0° C. The mixture was warmed to ambient temperature, stirred for 45 min, and filtered through a thin pad of silica gel (EtOAc). The filtrate was concentrated and dissolved in 10 mL of ether. This ether solution was added to a mixture of $AlCl_3$ (120 mg, 0.9 mmol) and $LiAlH_4$ (1 mL of a 1 M solution in ether) in 5 mL of ether at ambient temperature. The mixture was stirred overnight and an aqueous solution of NaOH (15%) was added to the mixture dropwise until a white suspension was formed, and was filtered through a pad of Celite. The filtrate was concentrated and chromatographed (5%-10% MeOH in $CHCl_3$) to give 6 mg (35%) of SR 16233. The identity of the product was confirmed using $^1$H NMR spectroscopy, and the NMR spectrum is shown in FIG. 15. The mass spectrum is shown in FIG. 16.

Figure 17:
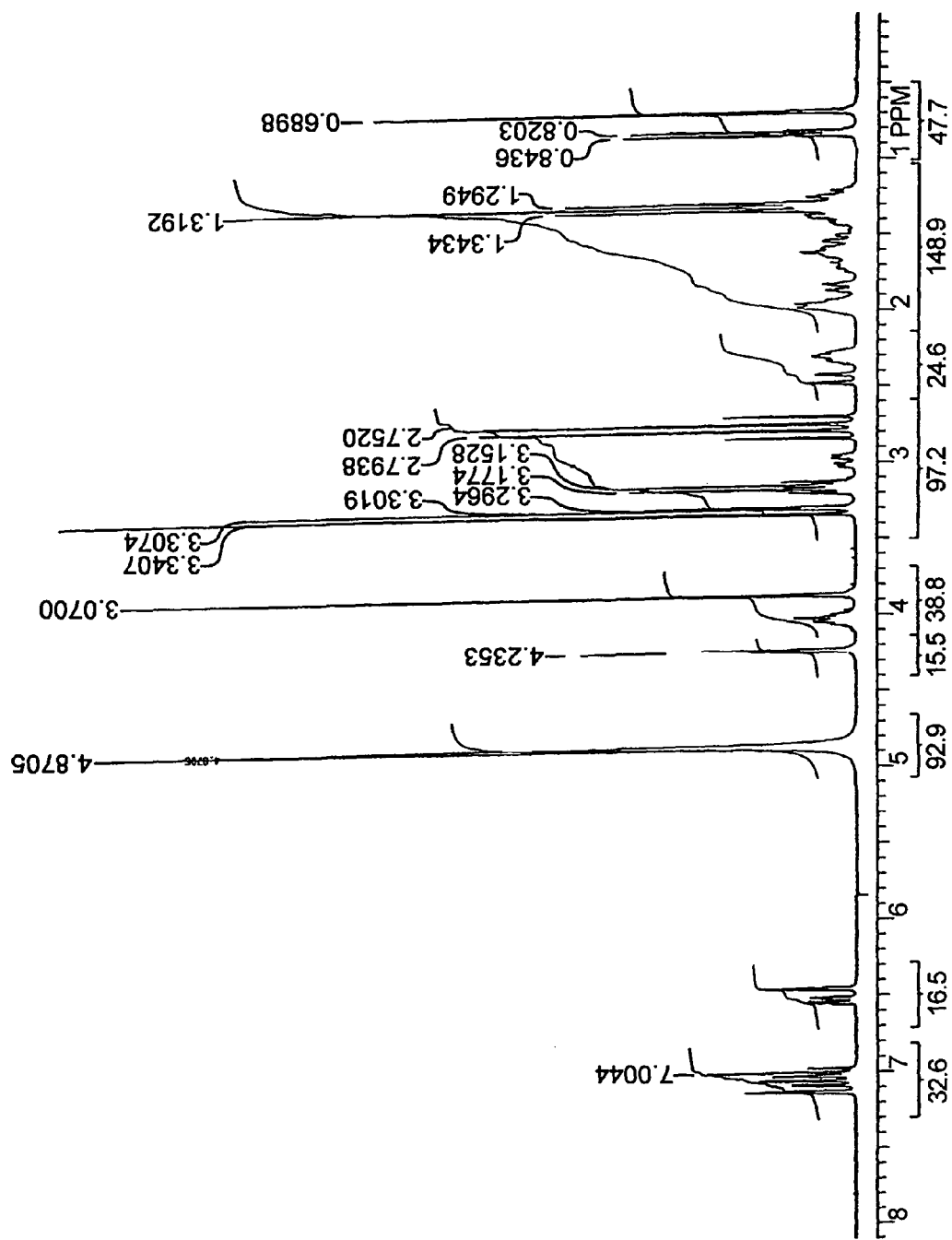
FIG. 17 is a $^1H$ NMR spectrum of compound SR 16234, the structure of which is shown in FIGS. 2 and 3 (synthesized as described in Example 2).
Figure 18:
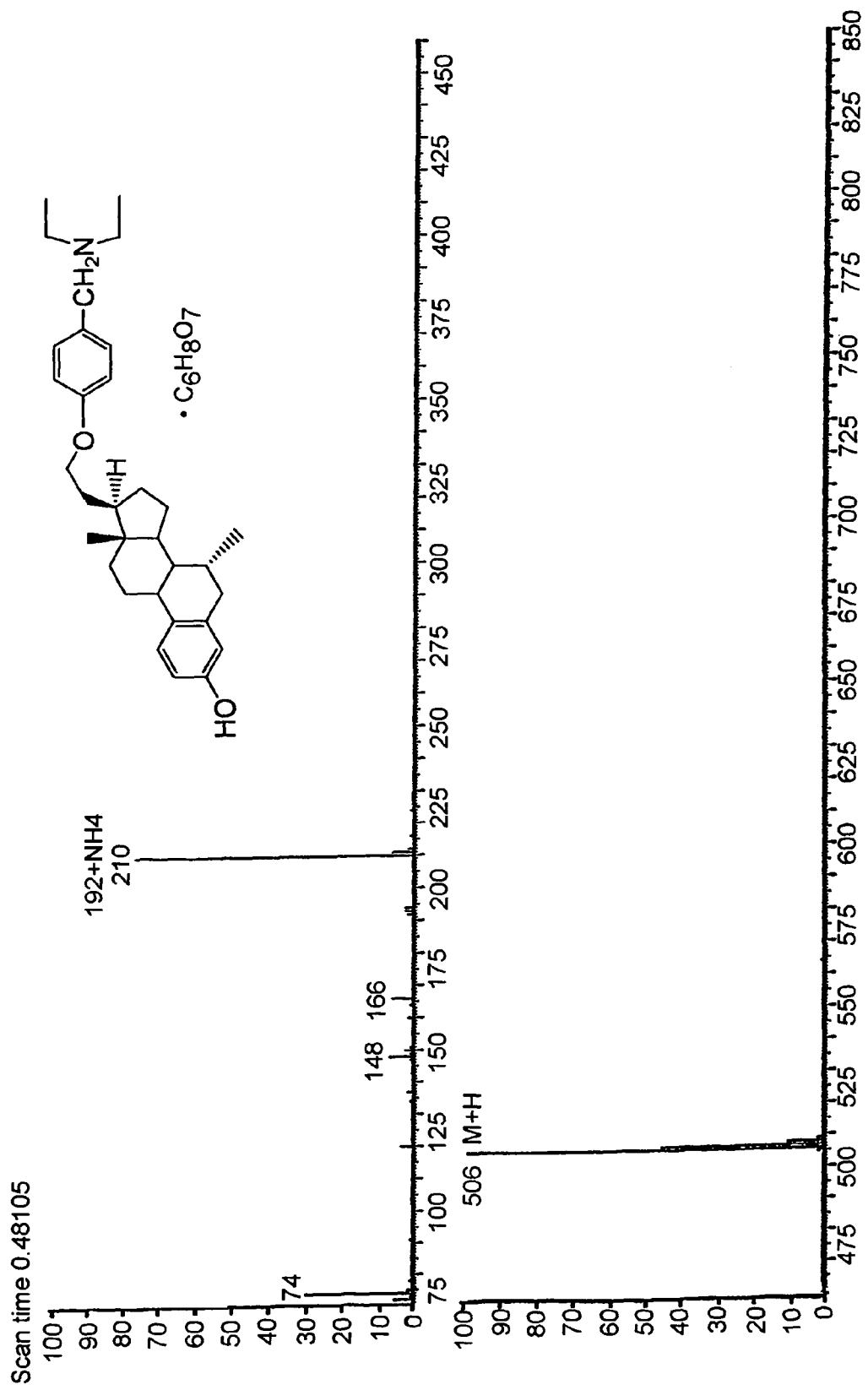
FIG. 18 is a mass spectrum of compound SR 16234.

Citrate salt of 3-hydroxy-7α-methyl-21-[2'-methoxy-4'-(N,N-diethylamino-methyl)phenoxy]-pregna-1,3,5(10)-triene (SR 16234): The free base SR 16233 (240.5 g, 0.476 mol) was dissolved in a total volume of methanol (1.700 mL, ~7 mL/g of base). To the hot solution was added citric acid (93.5 g, 0.487 mol) (2% excess). The combined clear reaction mixture was stirred and crystallization started and quickly proceeded. Finally, the reaction mixture was left overnight. The crystalline material was filtered off and then washed with a small amount of cold methanol and ether. The crystalline material was dried under vacuum to give 309.0 g or 93% product as an off-white powder, m.p. 154-155 C. The $^1$H NMR spectrum is shown in FIG. 17, and the mass spectrum is shown in FIG. 18.

EXAMPLE 3

Synthesis of 3-hydroxy-7α-methyl-21-[21-methoxy-4'-(diethylaminomethyl)-phenoxy]-19-norpregna-1,3,5(10)triene citrate ("SR 16234") from 21-hydroxy-19-norpregna-4-en-3-one, method 2

SR 16234 was synthesized from 21-hydroxy-19-norpregna-4-en-3-one (3) as illustrated in FIG. 3, using the following procedure.

Synthesis of (7): To a mixture of 1.512 g (5 mmol) of 3 (synthesized in Example 1) and 1.06 g (10.5 mmol) of $Et_3N$ in 25 mL of sulfolane was added 1.03 g (9 mmol) of MsCl dropwise at ambient temperature, and then stirred for 30 min.

Figure 19:
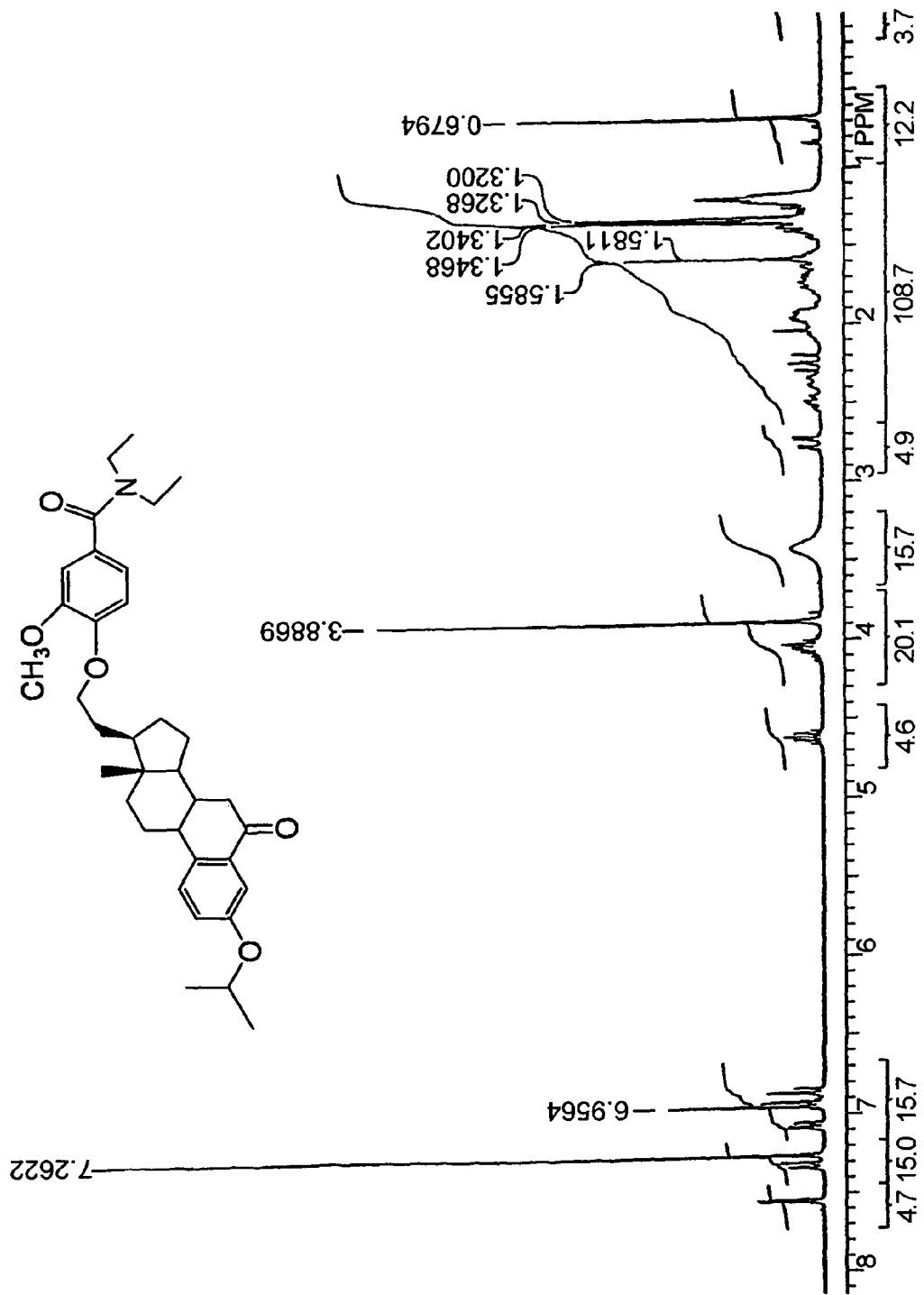
FIG. 19 is a $^1H$ NMR spectrum of compound 7, the structure of which is shown in FIGS. 2 and 3 (synthesized as described in Example 3).

To this mixture was added 1.34 g (6 mmol) of vanillic acid diethylamide and 1.96 g (6 mmol) of $Cs_2CO_3$. The resulting mixture was heated at 110-115° C. under a stream of air for 7 h, cooled to 85° C., and 2 mL of isopropyl bromide was added. The mixture was stirred for 1 h, and was diluted with ether and $CHCl_3$ (100 mL/20 mL), washed with water and brine, dried with sodium sulfate, concentrated, and chromatographed (5% acetone in $CH_2Cl_2$) to give 804 mg (27%) of 7 as a yellow glass. The identity of the product was confirmned using $^1H$ NMR spectroscopy. The NMR spectrum is shown in FIG. 19.

Synthesis of (6): To a solution of 302 mg (0.54 mmol) of 7 in 12 mL of THF was added 0.67 mL (1.35 mmol) of a 2.0 M solution of LDA in THF at 0° C. The mixture was stirred for 30 min, warmed to ambient temperature, and treated with 760 mg (5.4 mmol) of MeI. The resulting mixture was refluxed for 1.5 h, quenched into water, and extracted with ether (50 mL). The organic layer was dried (sodium sulfate), concentrated, and chromatographed (15% EtOAc in $CH_2Cl_2$) to give 233 mg (75%) of 6 as an oil.

SR 16233 and SR 16234 were then synthesized from 6 as described in Example 2.

EXAMPLE 4

Synthesis of 3-hydroxy-7α-methyl-21-[2'-methoxy-4'-(diethylaminomethyl)phenoxy-19-norpregna-1,3,5(10)triene citrate ("SR 16234") from 21-hydroxy-19-norpregna-4-en-3-one, method 3

SR 16234 was synthesized from 21-hydroxy-19-norpregna-4-en-3-one (3) as illustrated in FIG. 4, using the following procedure.

Synthesis of (8): To a suspension of alcohol 3 prepared in 84% yield from estrone (12.1 g, 40 mmol) in isopropenylacetate (120 mL) was added silica gel containing 3% sulfuric acid (0.55 g). This reaction mixture was heated at reflux for 4 h (after 2 h no change in TLC 30% EtOAc/hexane). The reaction mixture was filtered through a thin pad of celite/silica gel and the excess reagent was removed in vacuo. The residue became semisolid. The product was dried under high vacuum to give a crude yield (15.6 g or 100%). This compound was used in the synthetic step without further purification. NMR was in accordance with the proposed structure.

Synthesis of (9): Crude product 8 (~40 mmol) was dissolved into acetone (100 mL), water (32 mL), acetic acid (12 mL), and pyridine (7 mL), and to this solution was added sodium acetate (22.8 g). This mixture was cooled in an ice/water bath and N-bromo succinimide (8.9 g or 50 mmol) was added (protected from light). The combined reaction mixture was stirred at 0 to +5° C. for 3 h. TLC (20% EtOAc/hexane) showed no starting material. The reaction mixture was poured into an ice cold sat. sodium chloride solution. This mixture was extracted 3 times with ether. The combined ether solution was washed with sat. sodium chloride solution, dried over $Na_2SO_4$, and evaporated in vacuo to give the crude brominated product. This product was dehydrobrominated in the following way. The bromo compound was dissolved into DMF (72 mL). This solution was added to a hot suspension of lithium bromide (11.6 g) and lithium carbonate (11.6 g) in DMF (300 mL). The reaction mixture was heated at reflux for 1 h. The reaction mixture was cooled and filtered and the residue was washed with some DMF. The filtrate and the washings were combined and added to ice/water. The aqueous solution was extracted with ether 3 times. The combined either solution was washed with sodium bicarbonate solution 4% and water and dried over sodium sulfate and concentrated to a syrup. The crude material was purified on a silica gel column, eluted with 25% ethyl acetate/hexanes. Yield after recrystallization from ethyl acetate 8.4 g, 62% from the 21-alcohol 3. NMR and MS were in agreement with the proposed structure.

Synthesis of (10): To a stirred suspension of cuprous iodide (4.16 g, 22 mmol) in dry ether (30 mL), was added a 1.5 M methyl lithium, lithium bromide complex in ether (20.0 mL, 30 mmol). To this solution, cooled to 0-5° C. was added the steroid acetate 9 (2.5 g, 7.3 mmol) dissolved into ether (30 mL) over a period of 10 min. Stirring was continued for an additional 15 min and then the reaction mixture was quenched with a saturated ammonium chloride solution. The aqueous phase was separated and extracted twice with ether. The combined organic phase was washed twice with ammonium chloride solution and then water and dried over $MgSO_4$. Evaporation of the solvent gave the crude material as a gum. Treatment of the crude material with p-toluene sulfonic acid in dichloromethane gave the target compound in a yield of 1.8 g, 69%. NMR and MS were in agreement with the proposed structure.

Figure 20:
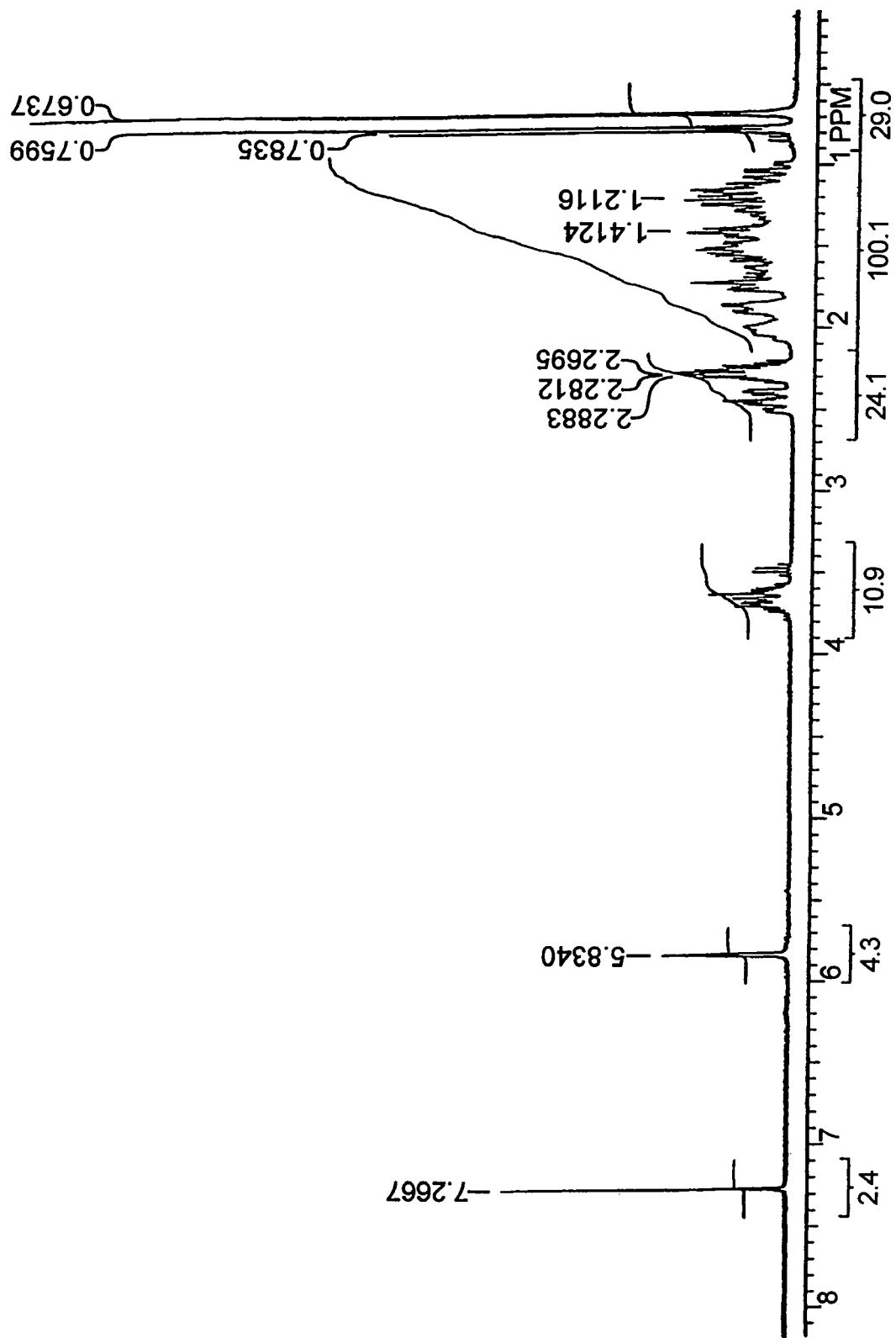
FIG. 20 is a $^1H$ NMR spectrum of compound 11, the structure of which is shown in FIG. 4 (synthesized as described in Example 4).

Synthesis of (11): To the acetate 10 (0.53 g, 1.48 mmol) dissolved into methanol (20 mL) was added KOH (40 mg) and the reaction mixture was stirred at room temperature for 2 h. TLC showed complete reaction. The solvent was removed under reduced pressure. Water was added to the residue and the aqueous phase was extracted with ether 3 times. The combined ether phase was washed with saturated sodium chloride solution, dried over $Na_2SO_4$ and evaporated to give a gum (0.48 g). Addition of some ether induced crystallization. The crystals were collected to give 0.32 g of off-white (yellowish) crystals. Total yield 0.48 g, 100%. NMR and MS were in agreement with the proposed structure; the $^1H$ NMR spectrum of the product is shown in FIG. 20.

Figure 21:
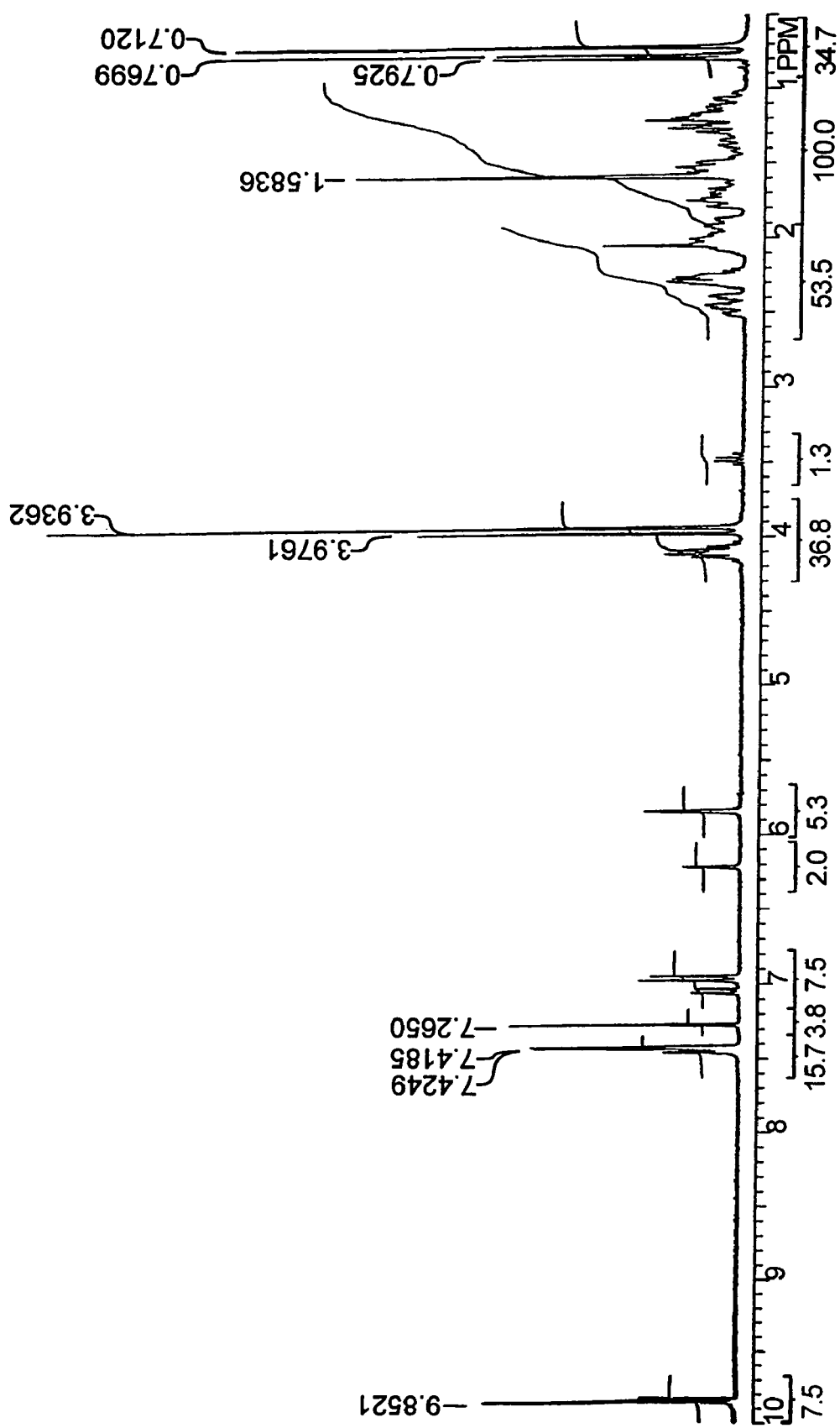
FIG. 21 is a $^1H$ NMR spectrum of compound 12, the structure of which is shown in FIG. 4 (synthesized as described in Example 4).

Synthesis of (12): A mixture of the steroid alcohol 11 (0.30 g, 0.95 mmol), vanillin (0.310 g, 2.04 mmol), and triphenylphosphine (0.53 g, 2.04 mmol) was dissolved into THF (8 mL). To this solution was added dropwise a solution of diethylazadicarboxylate (0.37 g, 2.1 mmol). After stirring for 2 h the reaction was complete. Most of the solvent was evaporated and the total residue was chromatographed on a silica gel column and was eluted with 25% ethyl acetate/hexane. The fractions that contained the target compound were combined and evaporated to give 0.366 g of target compound. Yield 0.366 g, 85.5%. NMR and MS were in agreement with the proposed structure; the $^1H$ NMR spectrum of the product is shown in FIG. 21.

Figure 22:
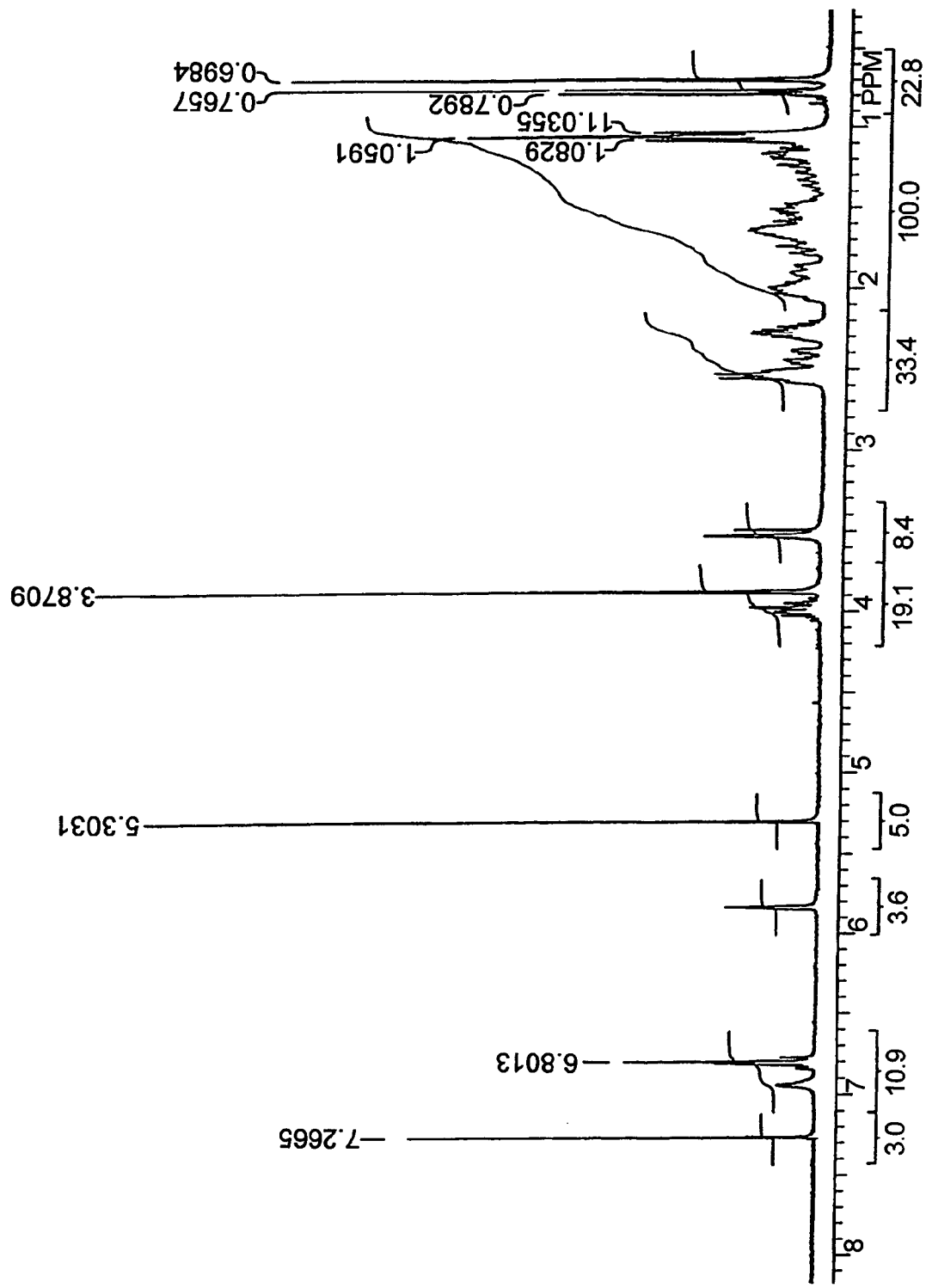
FIG. 22 is a $^1H$ NMR spectrum of compound 13, the structure of which is shown in FIG. 4 (synthesized as described in Example 4).
Figure 23:
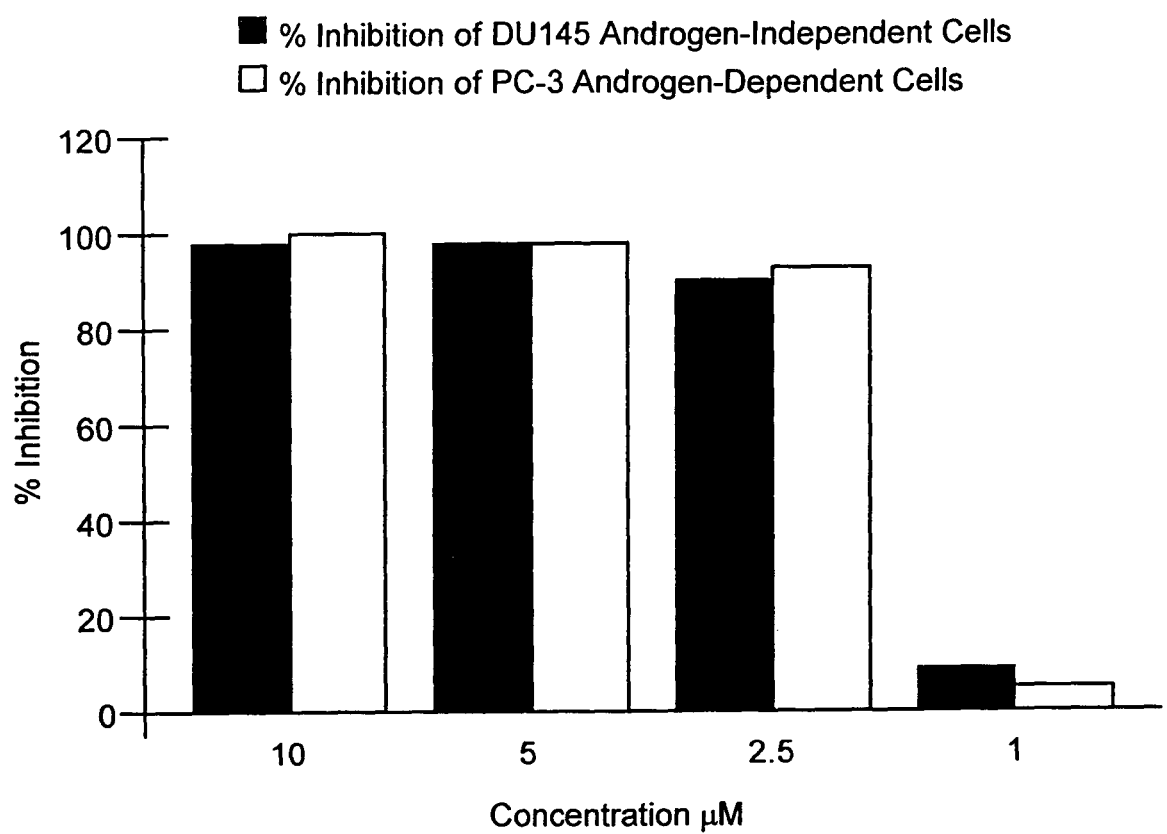
FIG. 23 is a graph illustrating the % inhibition versus concentration of SR 16312 as evaluated in an androgen-independent human prostate cancer assay, described in Example 7.

Synthesis of (13): To a stirred solution of the aldehyde 12 (0.150 g, 0.33 mmol) in dichloroethane (4 mL) was added diethylamine (0.68 mL, 0.66 mmol). After 15 min of stirring (the solution became reddish) sodium-triacetoxy borohydride (0.097 g or 0.46 mmol) was added in two portions. After stirring for 2 h the reaction was complete. The reaction mixture was diluted with some dichloromethane and was then poured into an aqueous solution of sodium bicarbonate (4%). The organic phase was separated and the aqueous phase was extracted once more with dichloromethane. The combined organic phase was washed with sodium bicarbonate solution and saturated sodium chloride solution was dried over $Na_2SO_4$. Evaporation of the solvent gave a syrup that was purified on a silica gel column and eluted with 5% methanol/dichloromethane. The fractions that contained the target compound were evaporated to give 0.113 g, 67% of pure target compound. NMR and MS were in agreement with the proposed structure; the $^1H$ NMR spectrum of the product is shown in FIG. 22.

Synthesis of SR 16233: To a stirred solution of 13 (0.085 g) in glacial acetic acid (3 ml) was added $CuCl_2$ (0.085 g). The mixture was stirred and heated at 100-105° C. for 24 hours. The reaction mixture was cooled and poured into ice-cold water. The aqueous phase was extracted twice with dichloromethane. The organic phase was washed with $NaHCO_3$ and water and was dried over $MgSO_4$. Evaporation of the solvent gave the target compound, which was then recrystallized from ethanol. Identity of the product, SR 16233, was confirmed using $^1H$ NMR spectroscopy.

EXAMPLE 5

Synthesis of 3-hydroxy-7α-methyl-21-[2'-methoxy-4'-(diethylaminomethyl)-phenoxy]-19-norpregna-1,3,5(10)triene citrate ("SR 16234") from 21-hydroxy-19-norpregna-4-en-3-one, method 4

Figure 5:
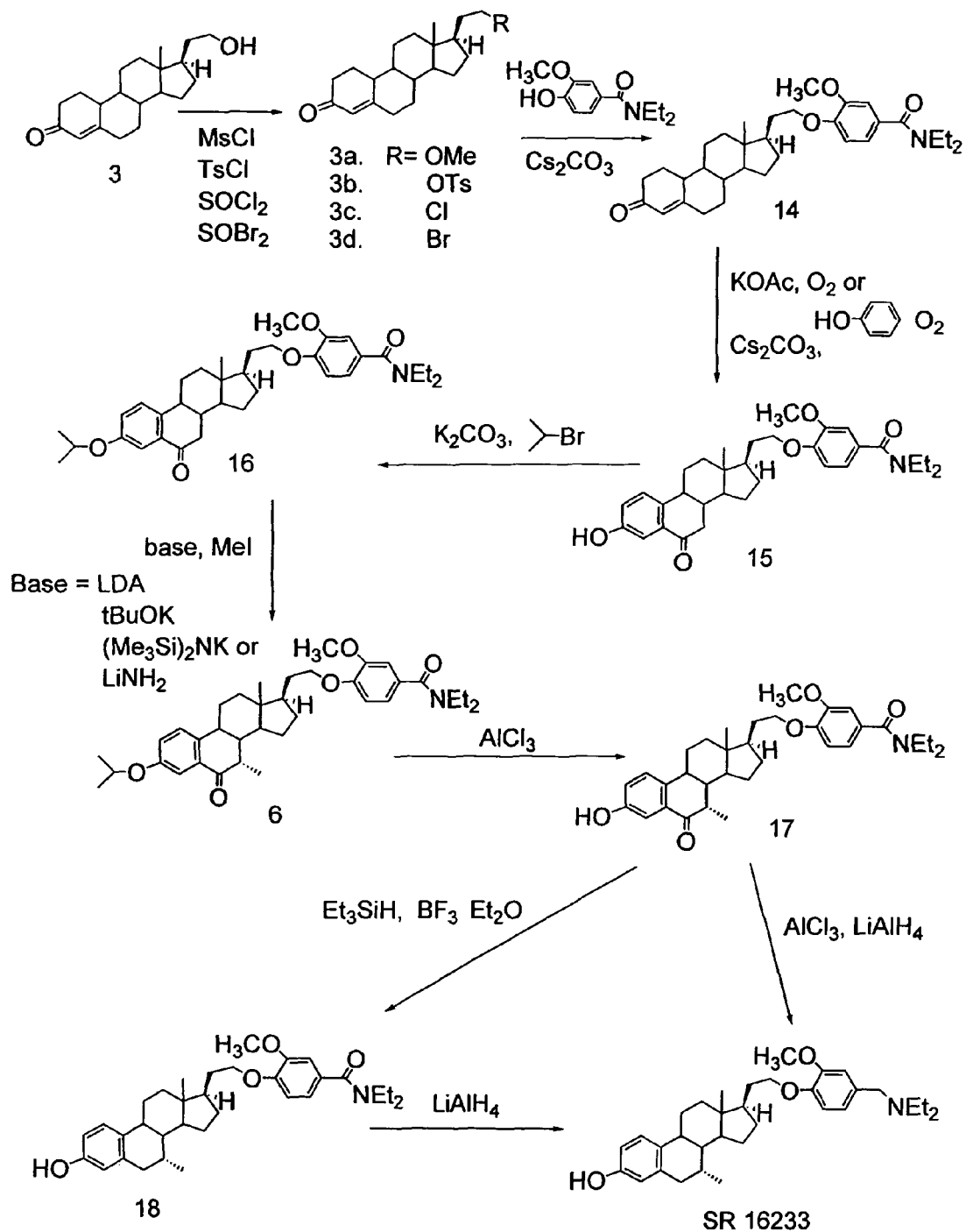
FIGS. 5, 6 and 7 are schemes illustrating alternative methods of the invention for synthesizing 3-hydroxy-7α-methyl-21-[2'-methoxy-4'-(diethylaminomethyl)-phenoxy]-19-norpregna-1,3,5(10)triene ("SR 16233"), the free amine precursor to SR 16234.
Figure 6:
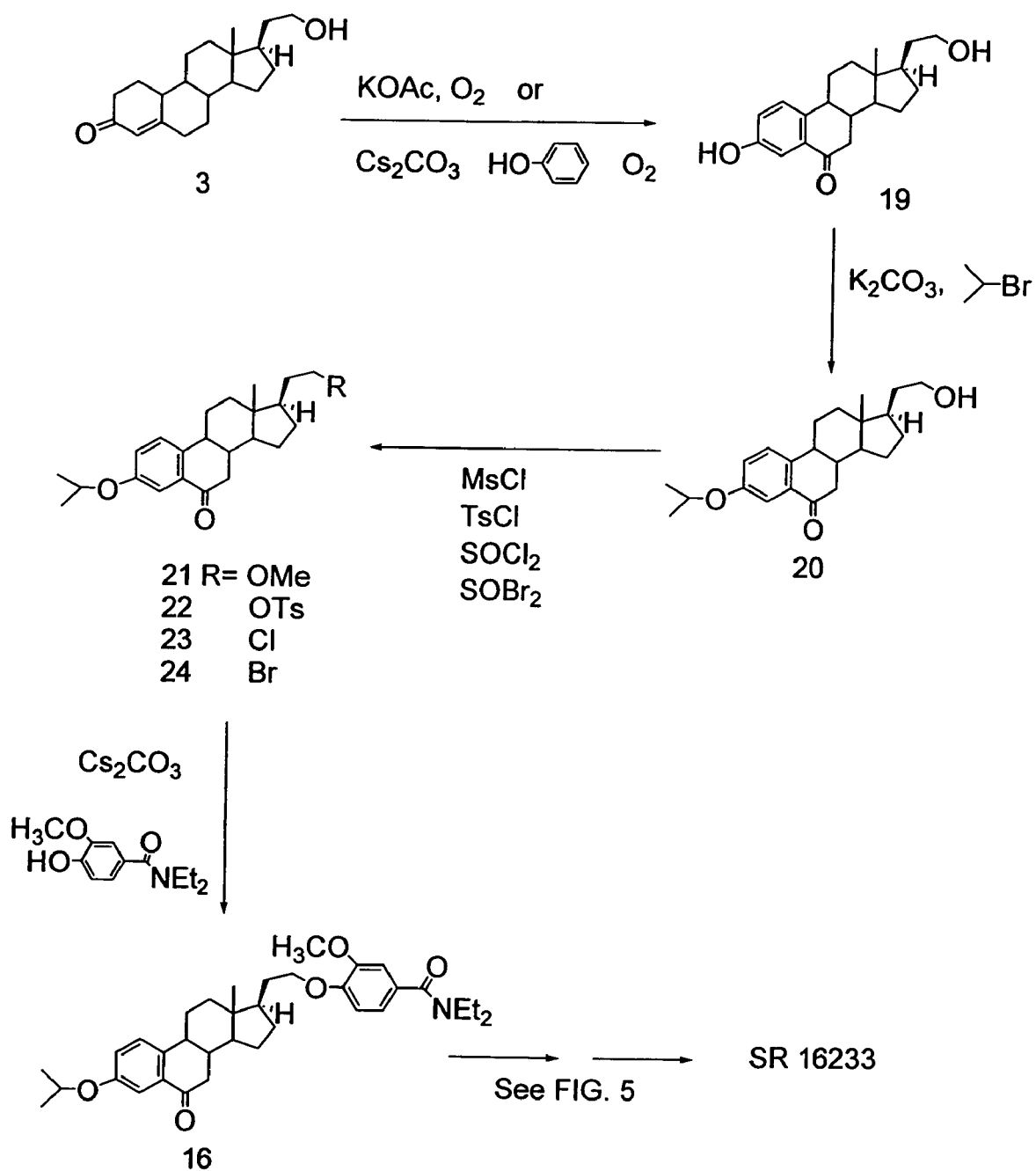
Figure 7:
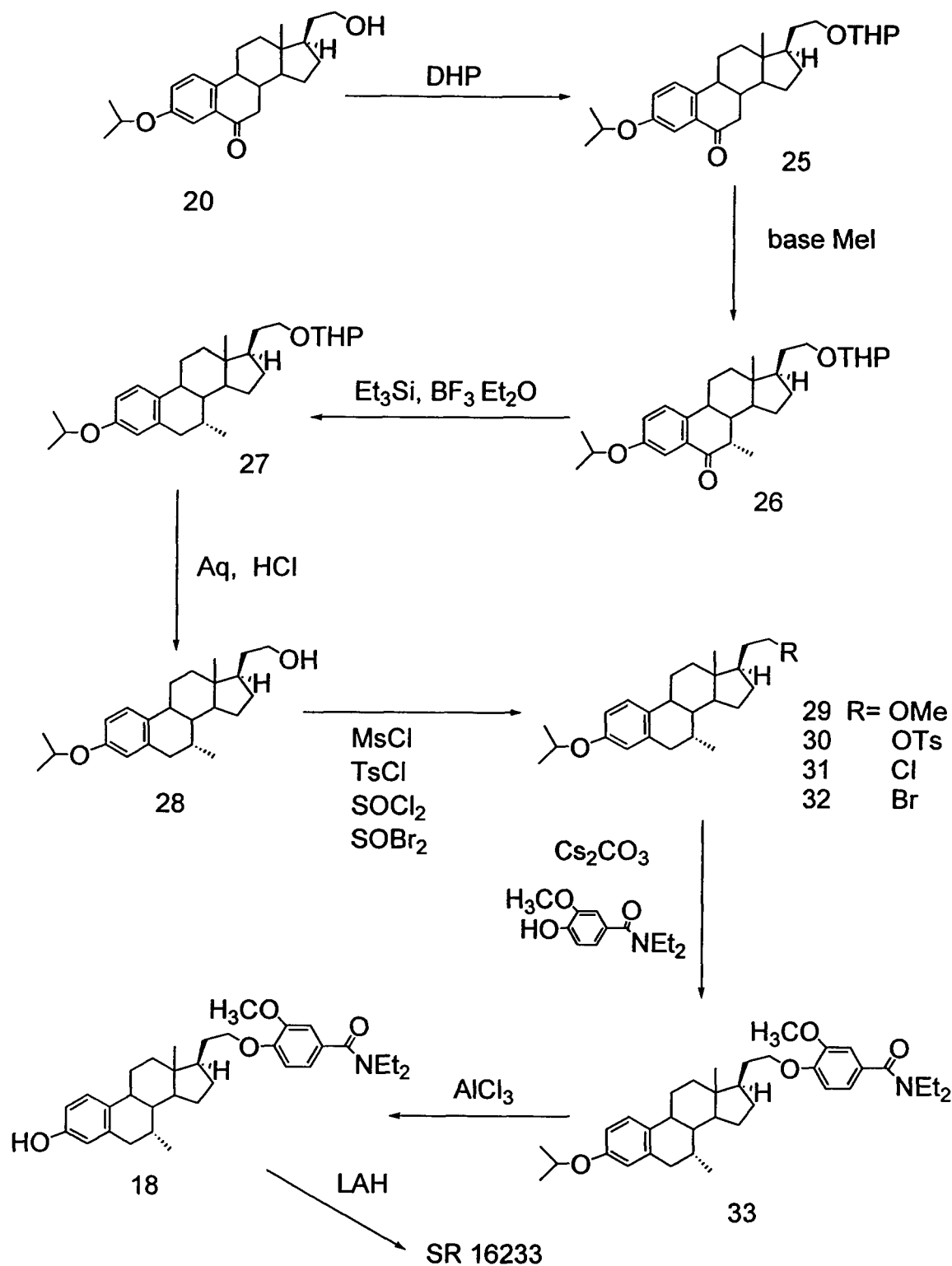

SR 16234 was synthesized from crude 21-hydroxy-19-norpregna-4-en-3-one (3) as illustrated in FIG. 5, using the following procedure.

Synthesis of 21-Hydroxy-19-norpregna-4-en-3-one 21-acetate (34): Crude product 3 prepared in Example 1 (18.0 g) was dissolved in pyridine (100 mL), and to this solution was added acetate anhydride (25 mL). The reaction was stirred at room temperature for 5 h and then poured into ice/water. The aqueous solution was extracted with ether twice. The combined ether extract was washed with water, ice-cold 4% hydrochloric acid solution, and water, and then dried over sodium sulfate and evaporated to give a semi-crystalline compound. This material was purified by chromatography to give 14.0 g of 35 (86%). $^1H$ NMR ($CDCl_3$) δ 0.66 (s, 3H), 2.04 (s, 3H), 4.06 (m, 2H), 5.83 (s, 1H).

Synthesis of 3,21-Dihydroxy-19-norpregna-3,5-dien-diacetate (8): To a suspension of 35 (12.1 g, 40 mmol) in isopropenylacetate (120 mL) was added silica gel containing 3% sulfuric acid (0.55 g). This reaction mixture was heated at reflux for 4 h, filtered through a thin pad of Celite, and excess reagent removed to give a semisolid product. The product was dried under high vacuum to give 15.6 g of crude product 8 (100%). The product from this reaction was used in the next step for the preparation of 21-hydroxy-19-norpregna-4,6-dien-3-on-21-acetate (37) without further purification. $^1H$ NMR ($CDCl_3$) was in accordance with the proposed structure.

Synthesis of 21-Hydroxy-19-norpregna-4,6-dien-3-on-21-acetate (9): Crude product 8 (15.6 g, ~40 mmol) was dissolved in a mixture of acetone (100 mL), water (32 mL), acetic acid (12 mL), and pyridine (7 mL), and to this solution was added sodium acetate (22.8 g). This mixture was cooled in an ice/water bath, and N-bromo-succinimide (8.9 g, 50 mmol) was added (protected from light). The combined reaction mixture was stirred at 0° to +5 C. for 3 h. The reaction mixture was poured into an ice-cold saturated sodium chloride solution and then extracted 3 times with ether and the ether extracts combined. The combined ether extract was washed with saturated sodium chloride solution, dried over $Na_2SO_4$, and evaporated under vacuum to give the crude brominated product. This product was dehydrobrominated as follows: the bromo compound was dissolved in dimethyl formamide (DMF, 72 mL) and then added to a hot suspension of lithium bromide (11.6 g) and lithium carbonate (11.6 g) in DMF (300 mL). The reaction mixture was heated at reflux for 1 h, then cooled and filtered. The residue was washed with DMF. The filtrate and the washings were combined and added to ice/water. The aqueous solution was extracted with ether three times and the extracts combined. The combined ether solution was washed with 4% sodium bicarbonate solution and water, dried over sodium sulfate, and concentrated to a syrup. The crude material was purified on a silica gel column eluting with 25% ethyl acetate/hexanes to yield, after recrystallization from ethyl acetate, 9.2 g (68%) of 9 from 8. $^1H$ NMR ($CDCl_3$) δ 0.69 (s, 3H), 2.05 (s, 3H), 4.08 (m, 2H), 5.78 (s, 1H), 6.20 (m, 2H). MS (DCI) m/z 343 (M+H).

Synthesis of 21-Hydroxy-7α-methyl-19-norpregna-4-en-3-on-21-acetate (10): To a stirred suspension of cuprous iodide (1.14 g, 6 mmol) in dry ether (25 mL) was added a 1.5 M (9.6 mmol) methyl lithium/lithium bromide complex in 6.4 mL of ether. This solution was cooled to 0-5° C., and then the acetate 9 (0.69 g, 2 mmol) dissolved in ether (40 mL) was added over a period of 10 min. Stirring was continued for an additional 15 min, and then the reaction mixture was quenched with a saturated ammonium chloride solution. The aqueous phase was separated and extracted three times with ether. The combined organic phase was washed twice with ammonium chloride solution and once with water, and then dried over $MgSO_4$. Evaporation of the solvent gave the crude material as a gum. Treatment of the crude material with p-toluenesulfonic acid in dichloromethane gave 0.48 g (67%) of crude acetate 10. $^1H$ NMR ($CDCl_3$) δ 0.67 (s, 3H), 0.78 (d, 3H), 2.05 (s, 3H), 4.06 (m, 2H), 5.83 (s, 1H). MS (DCI) m/z 359 (M+H).

Synthesis of 21-Hydroxy-7α-methyl-19-norpregna-1,3,5(10)-triene (35): To a solution of 10 (0.400 g, 1.04 mmol) in 4.5 mL of acetic acid was added copper(II) chloride (0.400 g). This reaction mixture was heated at 10° C. for 2 h. After 1 h, the reaction mixture was cooled and poured into water. The aqueous phase was extracted three times with ether. The combined ether phase was washed with water, sodium bicarbonate, and sodium chloride solution and then dried over sodium sulfate. Evaporation of the solvent gave the crude product in quantitative yield (some phenolic acetate seemed to be present). The crude material was hydrolyzed with potassium hydroxide in a mixture of methanol/water. Extraction with dichloromethane and evaporation of the solvent gave 0.28 g (85%) of purified material 35. $^1H$ NMR ($CDCl_3$) δ 0.59 (s, 3H), 0.78 (d, 3H), 3.55 (m, 2H), 6.48 (d, 1H), 6.58 (q, 1H), 7.09 (d, 1H).

Synthesis of 3,21-Dihydroxy-19-norpregna-1,3,5(10)-triene-bis-mesylate (36): Alcohol 35 (0.945 g, 3 mmol) was dissolved in dichloromethane (15 mL) and triethylamine (2.0 mL). This solution was cooled to 0-5° C. (ice/water bath), and methanesulfonyl chloride (0.90 g, 7.8 mmol) was added dropwise. The reaction mixture was stirred for 2 h at 0° C., then poured into ice/water. The dichloromethane was separated, and the water phase was extracted once more with dichloromethane. The dichloromethane was washed with water and then sodium chloride solution and dried over sodium sulfate. Evaporation of the solvent gave 1.34 g (95%) of 36 as a slightly sticky, white crystalline material. $^1H$ NMR was in agreement with the proposed structure. The crude material was used without further purification in the preparation of 37.

Synthesis of 3-Hydroxy-7α-methyl-21-(2'-methoxy-4'-N,N-diethylamido)phenoxy-19-norpregna-1,3,5(10)-triene-3-mesylate (37): To a solution-of 36 (1.20 g, 2.55 mmol) in 20 mL of DMF was added vanillic acid diethylamide (0.68 g, 3.06 mmol) and potassium carbonate (1.0 g, 3.06 mmol). The reaction mixture was heated at 90° C. for 2 h, then cooled to room temperature and poured into ice/water. Some crystalline material appeared and was filtered off. The aqueous phase was extracted with ether twice. The combined ether phase was washed with water and sodium chloride solution. Evaporation of the solvent gave 1.39 g (91%) of off-white material 37. $^1H$ NMR ($CDCl_3$) δ 0.68 (s, 3H), 0.86 (d, 3H), 3.13 (s, 3H), 3.89 (s, 3H), 3.95 (m, 2H), 6.8-7.05 (aromatic, 4H), 7.32 (d, 1H). MS (DCI) m/z 597 (M+H).

Synthesis of (SR 16233): A solution of crude 37 (0.500 g, 0.84 mmol) in ether (15 mL) was added dropwise to a suspension of LAH (0.160 g) in ether (10 mL). The reaction mixture was stirred overnight. The residue was poured into $CH_2Cl_2$. The $CH_2Cl_2$ phase was washed with water and then sodium chloride and evaporated to give a crude material that was purified by column chromatography to give 0.378 g (95%) of SR 16233. Identity of the product, SR 16233, was confirmed using $^1$H NMR spectroscopy. MS (DCI) m/z 505 (M+H).

Synthesis of SR 16234: The free base SR 16233 (240.5 g, 0.476 mol) was dissolved in methanol (total volume 1.700 mL, ~7 mL/g of base). To the hot solution was added citric acid (93.5 g, 0.487 mol) (2% excess). As the clear reaction mixture was stirred, crystallization began and proceeded fast. Finally the reaction mixture was left overnight. The crystalline material was filtered off and washed with a small amount of cold methanol and ether. The crystalline material was dried under vacuum to give 316 g of SR 16234 (95%).

EXAMPLE 6

Synthesis of 3-hydroxy-7α-methyl-21-[2'-methoxy-4'-(diethylaminomethyl)-phenoxy]-19-norpregna-1,3,5(10)triene citrate ("SR 16234") from 21-hydroxy-19-norpregna-4-en-3-one, method 5

SR 16234 was synthesized from crude 21-hydroxy-19-norpregna-4-en-3-one (3) as illustrated in FIG. 9, using the following procedure.

Synthesis of (20): To a solution of 1.125 g (3.7 mmol) of crude product 3 in 60 mL of isopropanol was added 0.188 g (0.7 mmol) of iodine. The resulting mixture was refluxed under a stream of oxygen for 2 h, then cooled to room temperature. The mixture was diluted with ether (150 mL), washed with water and then brine, dried, and concentrated to give an oil. Chromatographic separation (40% EtOAc in hexanes) gave 0.814 g (61%) of 20. $^1$H NMR (CDCl$_3$) δ 0.64 (s, 3H), 1.32 (d, 3H, J=1.9 Hz), 1.34 (d, 3H, J=1.9 Hz), 2.77 (dd, 1H, J=16.8 Hz, 3.3 Hz), 3.68 (m, 2H), 4.61 (m, 1H), 7.07 (dd, 1H, J=8.4 Hz, 3.0 Hz), 7.33 (d, 1H, J=8.4 Hz), 7.55 (d, 1H, J=3.0 Hz).

Synthesis of (4): To a solution of 0.814 g (2.3 mmol) of 20 in 20 mL of $CH_2Cl_2$ was added 5 mL of dihydropyran (DHP) and 0.05 g of pyridium p-toluenesulfonate. The mixture was stirred at room temperature for 2 h, and Et$_3$N (0.5 mL) was added. The mixture was diluted with ether (30 mL), washed with water and then brine, dried, and concentrated to give 1.01 g (100%) of (4), which was used in the next reaction without purification. $^1$H NMR (CDCl$_3$) δ 0.64 (s, 3H), 1.32 (d, 3H, J=1.9 Hz), 1.34 (d, 3H, J=1.9 Hz), 2.76 (dd, 1H, J=16.8 Hz, 3.3 Hz), 3.35-3.91 (m, 4H), 4.10 (m, 2H), 7.07 (dd, 1H, J=8.4 Hz, 3.0 Hz), 7.33 (d, 1H, J=8.4 Hz), 7.55 (d, 1H, J=3.0 Hz). MS (DCI) m/z 441 (M+H).

Synthesis of (5): To a solution of 0.660 g (1.5 mmol) of 4 in 25 mL of THF was added 2.25 mL (4.5 mmol) of a 2.0 M solution of lithium diisopropyl amide (LDA) in THF at 0° C. The mixture was stirred for 40 min, warmed to room temperature, and treated with 1 mL of MeI. The resulting mixture was refluxed for 40 min, then cooled to 0° C. Methanol (10 mL) and TsOH (1 g) were added, and the mixture was stirred for 2 h. The mixture was diluted with ether (50 mL), washed with saturated NaHCO$_3$ and then brine, dried, concentrated, and chromatographed (25% EtOAc in hexanes) to give 0.447 g (80%) of (5). $^1$H NMR (CDCl$_3$) δ 0.64 (s, 3H), 1.11 (d, 3H, J=7.6 Hz), 1.32 (d, 3H, J=1.5 Hz), 1.34 (d, 3H, J=1.5 Hz), 3.70 (m, 2H), 4.61 (m, 1H), 7.07 (dd, 1H, J=8.4 Hz, 3.0 Hz), 7.33 (d, 1H, J=8.4 Hz), 7.55 (d, 1H, J=3.0 Hz).

Synthesis of (28): To a solution of 0.225 g (0.6 mmol) of 5 in 30 mL of methanol was added 0.050 g of 10% Pd/C. The mixture was hydrogenated under 3 atm. of H$_2$ for 22 h, then filtered through a thin pad of silica gel. The filtrate was concentrated and chromatographed (20% EtOAc in hexanes) to give 0.168 g (77%) of 28. $^1$H NMR (CDCl$_3$) δ 0.64 (s, 3H), 0.84 (d, 3H, J=7.1 Hz), 1.32 (d, 3H, J=1.9 Hz), 1.34 (d, 3H, J=1.9 Hz), 3.69 (m, 2H), 4.61 (m, 1H), 6.61-6.73 (m, 2H), 7.21 (m, 1H).

Synthesis of (35): To a solution of 0.108 g (0.3 mmol) of 28 in 20 mL of $CH_2Cl_2$ was added 0.120 g (0.9 mmol) of AlCl$_3$ at room temperature. The resulting mixture was stirred for 2.5 h, then filtered through a thin pad of silica gel (with ether as eluent). The filtrate was concentrated to give 0.084 g (92%) of 35. $^1$H NMR (CDCl$_3$) δ 0.64 (s, 3H), 0.84 (d, 3H, J=7.1 Hz)l, 3.69 (m, 2H), 6.60-6.72 (m, 2H), 7.22 (m, 1H).

Synthesis of (36): Alcohol 35 (0.945 g, 3 mmol) was dissolved in dichloromethane (15 mL) and triethylamine (2.0 mL). This solution was cooled to 0-5° C. (ice/water bath), and methanesulfonyl chloride (0.90 g, 7.8 mmol) was added dropwise. The reaction mixture was stirred for 2 h at 0° C., then poured into ice/water. The dichloromethane was separated, and the water phase was extracted once more with dichloromethane. The dichloromethane was washed with water and then sodium chloride solution and dried over sodium sulfate. Evaporation of the solvent gave 1.34 g (95%) of 36 as a slightly sticky, white crystalline material. $^1$H NMR was in agreement with the proposed structure. The crude material was used without further purification in the preparation of 37.

Synthesis of (37): To a solution of 36 (1.20 g, 2.55 mmol) in 20 mL of DMF was added vanillic acid diethylamide (0.68 g, 3.06 mmol) and potassium carbonate (1.0 g, 3.06 mmol). The reaction mixture was heated at 90° C. for 2 h, then cooled to room temperature and poured into ice/water. Some crystalline material appeared and was filtered off. The aqueous phase was extracted with ether twice. The combined ether phase was washed with water and sodium chloride solution. Evaporation of the solvent gave 1.39 g (91%) of off-white material 37. $^1$H NMR (CDCl$_3$) δ 0.68 (s, 3H), 0.86 (d, 3H), 3.13 (s, 3H), 3.89 (s, 3H), 3.95 (m, 2H), 6.8-7.05 (aromatic, 4H), 7.32 (d, 1H). MS (DCI) m/z 597 (M+H).

Synthesis of SR 16233: A solution of crude 37 (0.500 g, 0.84 mmol) in ether (15 mL) was added dropwise to a suspension of LAH (0.160 g) in ether (10 mL). The reaction mixture was stirred overnight. The residue was poured into $CH_2Cl_2$. The $CH_2Cl_2$ phase was washed with water and then sodium chloride and evaporated to give a crude material that was purified by column chromatography to give 0.378 g (95%) of SR 16233. Identity of the product, SR 16233, was confirmed using $^1$H NMR spectroscopy. MS (DCI) m/z 505 (M+H).

Synthesis of SR 16234: The free base SR 16233 (240.5 g, 0.476 mol) was dissolved in methanol (total volume 1.700 mL, ~7 mL/g of base). To the hot solution was added citric acid (93.5 g, 0.487 mol) (2% excess). As the clear reaction mixture was stirred, crystallization began and quickly proceeded. Finally the reaction mixture was left overnight. The crystalline material was filtered off and washed with a small amount of cold methanol and ether. The crystalline material was dried under vacuum to give 316 g of SR 16234 (95%).

EXAMPLE 7

Biological Evaluation:

Compound SR 16312, having the structural formula

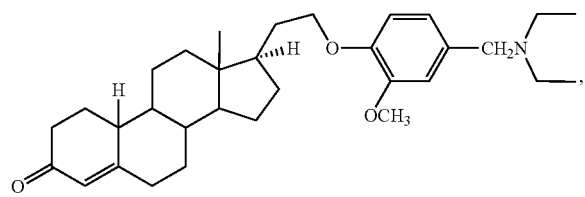

was synthesized as described in Example 4 without methylation at the 7-position of the steroid nucleus. The compound was evaluated for its inhibitory effect on androgen-independent human prostate cancer cells, DU145 cells and PC-3 cells, in a standard in vitro androgen-independent human prostate cancer assay.

DU145 and PC-3 human prostate cancer cell lines were obtained from the American Type Culture Collection, Rockville, Md. Eagle's minimum essential medium, RPMI-1640 medium, fetal calf serum, nonessential amino acids, and sodium pyruvate were purchased from Sigma, St. Louis, Mo.

PC-3 cells were maintained in RPMI-1640 medium supplemented with 10% fetal calf serum (FCS) and DU145 cells in Eagle's minimum essential medium (MEM) supplemented with 10% FCS. 1% nonessential amino acids, and 1 mM pyruvate. All cells were cultured at 37° C. in a 5% $CO_2$/95% air atmosphere in 100% humidity. To initiate the growth inhibition assay, cells were seeded at 5000 cells per well in a 24-well plate in 500 µl of the appropriate medium for the individual cell line and cultured under the same conditions described above. Cells were allowed to attach for 24 hours, then test compound was added in 10 µl aliquots. The test compound was dissolved in DMSO first and diluted with medium. The final DMSO concentration was kept at 0.1%. Control cultures received vehicle alone. The medium in each well was changed every other day, with fresh test compound added. After 7 days of treatment, viable cells in each well were measured using the MTT assay as described in "Cellular Proliferation Assay," in *Protocols and Applications*, $3^{rd}$ Edition (Promega Corporation).

To perform the MTT assay, on Day 9, medium from each well was removed and 100 µl of fresh medium was added, followed by 15 µl of tetrazolium dye solution. The incubation was continued for 4 hours, and then 100 µl of solubilization/stop solution was delivered into each well. (During the four-hour incubation, viable cells converted the tetrazolium component of the dye solution to formazan, which gives a blue color.)

The plate was kept at room temperature overnight and the blue color measured at 575 nm on an ELISA plate reader. Based on the optical density of samples treated with the test compound and that of the control, the inhibitory effect of SR 16312 was evaluated. The results are set forth in FIG. 21. As may be seen in the figure, the compound resulted in virtually 100% inhibition at concentrations of 5 µM or higher.

EXAMPLE 8

7-αmethylation of 6-ketoestradiol using a THP protecting group

The stereoselective methylation of a 6-keto steroid according to the following scheme was accomplished as described below.

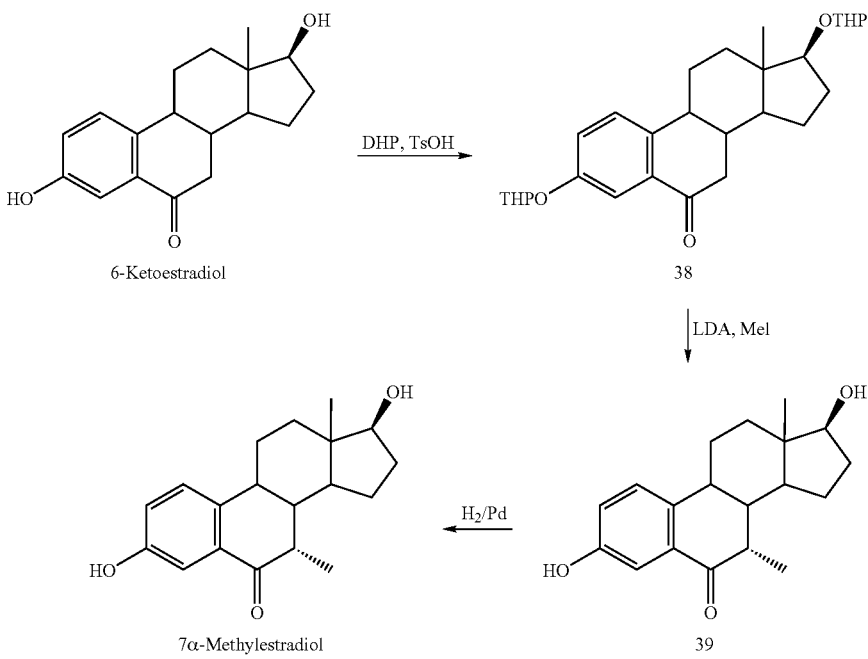

Synthesis of 3,17β-Dihydroxy-6-keto-estra-1,3,5(10) triene-3,17-ditetrahydropyranyl ether (38). To a solution of 0.100 gm of 6-ketoestradiol in 2.0 ml of dichloromethane was added 0.5 g of dihydropyran and 0.04 gm. of TsOH. The reaction was stirred for 18 h at room temperature under argon. The reaction was poured into 4% sodium bicarbonate and extracted with additional dichloromethane. The organic fractions were combined and dried over magnesium sulfate and evaporated to dryness to afford 0.157 gm (96% yield) of an oil 38. The reaction was not further purified and was used in the following reaction as is.

Synthesis of 3,17β-Dihydroxy-6-keto-7α-methyl-estra-1, 3,5(10) triene (39). To a solution of 0.140 g of diTHP analog 38 in 5 mL of dry tetrahydrofuran was added 0.47 mL of 2.0 M lithium diisopropylamide in 2.0 mL of tetrahydrofuran at room temperature. The reaction was stirred for 1.0 h. and then 0.25 mL of methyl iodide was added. The mixture was refluxed for 3.0 h., cooled to 0° C., and diluted with 5.0 mL of methanol. To this mixture was added 0.025 g of p-toluene sulfonic acid. The reaction mixture was stirred for an additional 2.0 h. Triethyl amine (1.0 ml) was then added and the reaction mixture evaporated at reduced pressure to yield 0.155 g of crude 39. The crude mixture was analyzed by NMR and showed only one isomer at C-7 as determined by the presence of only one doublet at 1.05 ppm. The crude product was diluted with chloroform and chromatographed on silica gel using 30% ethylacetate/hexane to afford pure 39 as an oil. $^1$H NMR 7.36-7.0 (m, 3H, aromatic), 3.70 (t, 1H, 17-H) 1.05 (d, J=7.5 Hz., 7α-CH$_3$) 0.74 (s, 18-CH$_3$)

Synthesis of 7α-Methylestradiol: Compound 39 may be converted into 7α-methylestradiol using standard reaction conditions. For example, 10% Pd/C can be to a solution of 39 in methanol and then hydrogenated under 3 atm. of H$_2$ for several hours. The hydrogenated product may then be collected by filtration through a thin pad of silica gel.

We claim:

1. A compound having the structural formula (III)

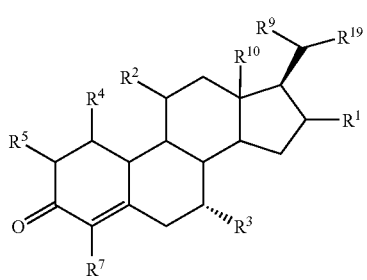

wherein:
R$^1$ is hydrogen or CR$^{11}$R$^{12}$, wherein R$^{11}$ and R$^{12}$ are hydrogen or lower alkyl;
R$^2$ is selected from the group consisting of hydrogen, hydroxyl, alkyl, —OR$^{13}$, and —SR$^{13}$ wherein R$^{13}$ is alkyl;
R$^3$ is selected from the group consisting of hydrogen and lower alkyl;
R$^4$, R$^5$, and R$^7$ are independently hydrogen or lower alkyl;
R$^9$ is hydrogen;
R$^{10}$ is methyl or ethyl; and
R$^{19}$ is hydroxyl, hydroxymethyl, protected hydroxyl, protected hydroxymethyl, activated hydroxyl, or activated hydroxylmethyl.

2. The compound of claim 1, having the structural formula (IV)

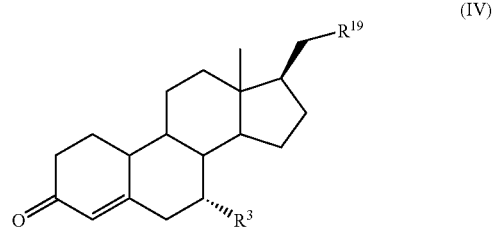

wherein:
R$^3$ is hydrogen or lower alkyl; and
R$^{19}$ is hydroxyl, hydroxymethyl, —O-acetyl, or —O-tetrahydropyranyl.

3. The compound of claim 2, wherein R$^3$ is hydrogen or methyl, and R$^{19}$ is hydroxymethyl.

4. The compound of claim 3, wherein R$^3$ is hydrogen.

5. The compound of claim 3, wherein R$^3$ is methyl.

6. The compound of claim 2, wherein R$^3$ is hydrogen or methyl, and R$^{19}$ is hydroxyl.

7. The compound of claim 6, wherein R$^3$ is hydrogen.

8. The compound of claim 6, wherein R$^3$ is methyl.

9. A method for synthesizing a compound, comprising treating a starting material having the structural formula (I)

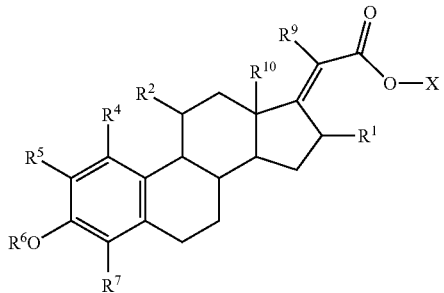

with an alkali metal in the presence of ammonia or an alkylamine, wherein, in formula (I), X is lower alkyl;
R$^1$ is CR$^{11}$R$^{12}$, wherein R$^{11}$ and R$^{12}$ are hydrogen or lower alkyl;
R$^2$ is selected from the group consisting of hydrogen, hydroxyl, alkyl, —OR$^{13}$, and —SR$^{13}$ wherein R$^{13}$ is alkyl;
R$^4$, R$^5$, R$^6$, and R$^7$ are independently selected from the group consisting of hydrogen and lower alkyl;

$R^9$ is hydrogen or hydrocarbyl; and
$R^{10}$ is methyl or ethyl, resulting in a reaction product having the structural formula (VIII)
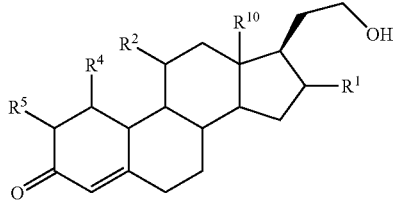
10. A method for synthesizing 21-hydroxy-19-norpregna-4-en-3-one, comprising treating (IX)
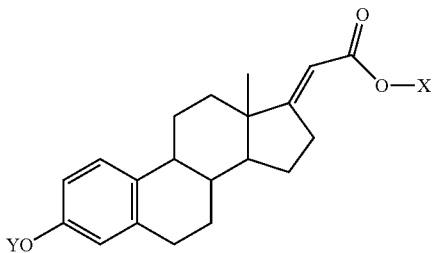
wherein X and Y are independently lower alkyl, with an alkali metal in the presence of ammonia or an alkylamine.
* * * * *